(12) United States Patent
Blott et al.

(10) Patent No.: US 7,407,750 B2
(45) Date of Patent: Aug. 5, 2008

(54) MARKER ASSISTED SELECTION OF BOVINE FOR IMPROVED MILK COMPOSITION

(76) Inventors: Sarah Blott, Department of Genetics, Faculty of Veterinary Medicine, University of Liege, 20 Boulevard de Colonster, B-4000 Liege (BE); Jong-Joo Kim, Department of Genetics, Faculty of Veterinary Medicine, University of Liege, 20 Boulevard de Colonster, B-4000 Liege (BE); Anne Schmidt-Kuntzel, Department of Genetics, Faculty of Veterinary Medicine, University of Liege, 20 Boulevard de Colonster, B-4000 Liege Anne Cornet, Department of Genetics, Faculty of Veterinary Medicine, University of Liege, 20 Boulevard de Colonster, B-4000 Liege (BE); Paulette Berzi, Department of Genetics, Faculty of Veterinary Medicine, University of Liege, 20 Boulevard de Colonster, B-4000 Liege (BE);

(Continued)

( * ) Notice: Subject to any disclaimer, the term of this patent is extended or adjusted under 35 U.S.C. 154(b) by 265 days.

(21) Appl. No.: 10/473,683

(22) PCT Filed: Aug. 16, 2002

(86) PCT No.: PCT/NZ02/00157
§ 371 (c)(1),
(2), (4) Date: Aug. 9, 2004

(87) PCT Pub. No.: WO03/104492

PCT Pub. Date: Dec. 18, 2003

(65) Prior Publication Data
US 2004/0254104 A1 Dec. 16, 2004

(30) Foreign Application Priority Data
Jun. 5, 2002 (NZ) ..................... 519372
Aug. 15, 2002 (NZ) ..................... 520797

(51) Int. Cl.
C12Q 1/68 (2006.01)
C12P 19/34 (2006.01)
C07H 21/04 (2006.01)

(52) U.S. Cl. ............... 435/6; 435/91.2; 536/23.1; 536/24.3

(58) Field of Classification Search ............... None
See application file for complete search history.

(56) References Cited

OTHER PUBLICATIONS

GenBank Locus AF044258, GI:2854046, (Feb. 11, 1998) 'Bos taurus somatotropin receptor 1B precursor, mRNA, complete cds.' pp. 1-2.*

Aggrey SE et al 'Markers within the regulatory region of the growth hormone receptor gene and their association with milk-related traits in Holsteins.' J Hered. Jan.-Feb. 1999;90(1):148-51.☐☐.*

(Continued)

Primary Examiner—Ram R. Shukla
Assistant Examiner—Stephen Kapushoc
(74) Attorney, Agent, or Firm—Knobbe, Martens, Olson & Bear, LLP

(57) ABSTRACT

The present invention provides a method of genotyping bovine for improved milk production traits by determining the GHR genotypic state of said bovine, wherein the GHR gene and polymorphisms within said gene have been found to be associated with such improved milk production traits.

11 Claims, 7 Drawing Sheets

(76) Inventors: Nadine Cambisano, Department of Genetics, Faculty of Veterinary Medicine, University of Liege, 20 Boulevard de Colonster, B-4000 Liege (BE); Bernard Grisart, Department of Genetics, Faculty of Veterinary Medicine, University of Liege, 20 Boulevard de Colonster, B-4000 Liege (BE); Latifa Karim, Department of Genetics, Faculty of Veterinary Medicine, University of Liege, 20 Boulevard de Colonster, B-4000 Liege (BE); Patricia Simon, Department of Genetics, Faculty of Veterinary Medicine, University of Liege, 20 Boulevard de Colonster, B-4000 Liege (BE); Michel Georges, Department of Genetics, Faculty of Veterinary Medicine, University of Liege, 20 Boulevard de Colonster, B-4000 Liege (BE); Frederic Farnir, Department of Genetics, Faculty of Veterinary Medicine, University of Liege, 20 Boulevard de Colonster, B-4000 Liege (BE); Wouter Coppieters, Department of Genetics, Faculty of Veterinary Medicine, University of Liege, 20 Boulevard de Colonster, B-4000 Liege (BE); Sirja Moisio, Animal Production Research, Agriculture Research Centre MTT, FN-31500 Jokioinen (FI); Johanna Vilkki, Animal Production Research, Agriculture Research Centre MTT, FN-31500 Jokioinen (FI); Dave Johnson, Livestock Improvement Corporation, Cnr Ruakura & Morrinsonville Roads, Private Bag 3016, Hamilton (NZ); Richard Spelman, Livestock Improvement Corporation, Cnr Ruakura & Morrinsonville Roads, Private Bag 3016, Hamilton (NZ); Christine Ford, ViaLactia Biosciences (NZ) Ltd, Level 1, Unysis Building, 650 Great South Road, Penrose, PO Box 109185, Auckland (NZ); Russell Snell, ViaLactia Biosciences (NZ) Ltd, Level 1, Unysis Building, 650 Great South Road, Penrose, PO Box 109185, Auckland (NZ)

OTHER PUBLICATIONS

Hacker UT et al 'Lack of association between an interleukin-1 receptor antagonist gene polymorphism and ulcerative colitis.' Gut. May 1997;40(5):623-7.*
National Dairy Council 'ttable 7: Nutrient Composition of Mikls from Different Species', available online from www.nationaldairycouncil.org/NationalDairyCouncil/Nutrition/Products/table07.pdf.*
DePalm A 'Capturing Proteins Using Antibody Arrays' from Genomics and Proteomics, available online from author at www.adeplama.com, pp. 1-5.*
Thisted RA 'What is a P-value?' available online from www.stat.uchicage.edu/~thisted, pp. 1-6.*
Bork P et al 'Convergent evolution of similar enzymatic function on different protein folds: the hexokinase, ribokinase, and galactokinase families of sugar kinases.' Protein Sci. Jan. 1993;2(1):31-40.*
Juppner H 'Functional properties of the PTH/PTHrP receptor.' Bone. Aug. 1995;17(2 Suppl):39S-42S.*
Luct MC et al 'Expression of somatotropin receptor messenger ribonucleic acid in bovine tissues.' J Dairy Sci. Jul. 1998;81(7):1889-95.*
Lucentini J 'Gene association studies typically wrong' The Scientist, Dec. 20, 2004, p. 20.*
GenBank Locus BTGHR, GI:510958, Feb. 11, 1997, pp. 1-2.□□.*
Landegren U et al 'A ligase-mediated gene detection technique.' Science. Aug. 26, 1988;241(4869):1077-80.*
Alignment of AF044258 : SID 4, pp. 1-4.*
Align BTGHR : Lucy et al, pp. 1-5.*
Goldsby et al. Immunology, Fifth Edition, section "Cross-Reactivity," p. 141.*
Alignemnt of AF044258 : SID2, from Blast 2 Sequences Results available online from www.ncbi.nlm.nih.gov, pp. 1-2.*
Falaki M. et al., "Relationships of polymorphisms for growth hormone and growth hormone receptor genes with milk production traits for Italian Holstein-Friesian Bulls," *J. Dairy Sci.* (1996) 79:1446-1453.
Moisio, S. et al., "Polymorphism within the 3' flanking region of the bovine growth hormone receptor gene," *Animal Genetics* (1998) 29(1):55-57.
Aggrey, S.E. et al., "Markers within the regulatory region of the growth hormone receptor gene and their association with milk-related traits in Holsteins" *The Journal of Heredity* (1999) 90(1):148-151.
Hoj, S. et al., "Growth hormone gene polymorphism associated with selection for milk fat production in lines of cattle," *Animal Genetics* (1993) 24(2):91-95.
Arranz, J.J. et al. (1998) "A QTL affecting milk yield and composition maps to bovine chromosome 20: a confirmation" *Animal Genetics* 29:107-115.
Georges, M. et al. (1995) "Mapping quantitative trait loci controlling milk production by exploiting progeny testing" *Genetics* 139:907-920.

* cited by examiner

```
ADARAFORAD  CCAGTTTCCATGGTTCTTAATTATTATCTT
            CCAGTTTCCATGGTTCTTAATTATTATCTTTGGAATACTTGGGCTAGCAGTG
A
ACATTATATTTACTCATATTTTCTAAACAGCAAAGGTAAGTGTGATATAACC
            ←——— GATTTGTCGTTTCCATTCACACTATATTGG  ADARAREVAD
```

Probe sequence is underlined.
Polymorphic site is in bold, and is either an A or T.

*Figure 6*

MARKER ASSISTED SELECTION OF BOVINE FOR IMPROVED MILK COMPOSITION

RELATED APPLICATIONS

This application is a National Phase under 35 U.S.C. 371 of the International Application PCT/NZ02/00157 filed Aug. 16, 2002 designating the US, which claims the benefit of priority of New Zealand Application No. 519372 filed Jun. 5, 2002, and New Zealand Application No. 520797 filed Aug. 15, 2002, all of which are expressly incorporated herein by reference in their entireties.

FIELD OF THE INVENTION

This invention relates to an application of marker assisted selection of bovine for a quantitative trait loci (QTL) associated with increased milk volume and improved milk composition, particularly although by no means exclusively, by assaying for the presence of at least one polymorphism in the gene which is associated with the QTL.

BACKGROUND

The genetic basis of bovine milk production is of immense significance to the dairy industry. An ability to modulate milk volumes and content has the potential to alter farming practices and to produce products which are tailored to meet a range of requirements. In particular, a method of genetically evaluating bovine to select those which express desirable traits, such as increased milk production and improved milk composition, would be desirable.

To date, bovine genomics are poorly understood and little is known regarding the genes which are critical to milk production. While there have been reports of quantitative trait loci (QTLs) on bovine chromosome 20 postulated to be associated with milk production (Georges et al (1995); Arranz et al (1998)), the specific genes involved have not to date been identified due to the poor mapping resolution of current experimental designs (e.g. Mackay 2001; Andersson 2001; Flint and Mott 2001; Mauricio, 2001). Strategies to improve the mapping resolution most often require breeding of large number of progeny to increase the density of cross-overs in the chromosome regions of interest (e.g. Darvasi, 1998). When working with humans or farm animals, this approach is not practical. An alternative approach is linkage disequilibrium (LD) mapping which aims at exploiting historical recombinants and has been shown in some livestock populations, including dairy cattle, to extend over very long chromosome segments when compared to human populations (Famir et al., 2000). However, long range LD is likely to result in a limited mapping resolution and the occurrence of association in the absence of linkage due to gametic association between non syntenic loci. Once mapped, a QTL can be usefully applied in marker assisted selection.

Marker assisted selection, which provides the ability to follow a specific favourable genetic allele, involves the identification of a DNA molecular marker or markers that segregate with a gene or group of genes associated with a QTL. DNA markers have several advantages. They are relatively easy to measure and are unambiguous, and as DNA markers are co-dominant, heterozygous and homozygous animals can be distinctively identified. Once a marker system is established, selection decisions are able to be made very easily as DNA markers can be assayed at any time after a DNA containing sample has been collected from an individual infant or adult animal, or even earlier as it is possible to test embryos in vitro if such embryos are collected.

The applicants have now identified a polymorphism in a gene associated with the QTL effect on bovine chromosome 20.

It is an object of the present invention to provide an application method for marker assisted selection of this polymorphism in the bovine gene which is associated with increased milk volume and altered milk composition; and/or to provide genetic markers for use in such a method; and/or to provide animals selected using the method of the invention as well as milk produced by the selected animals; and/or to provide the public with a useful choice.

SUMMARY OF THE INVENTION

This invention relates to the discovery of a polymorphism in the transmembrane domain of the growth hormone receptor gene which is associated with increased milk yield and altered milk composition, and flanking polymorphisms. The polymorphism in the transmembrane domain is also associated with a increase in live weight.

More specifically, the polymorphism in the bovine growth hormone receptor (GHR) gene coding sequence for the transmembrane domain results in a F279Y amino acid substitution (this is due to a single base change at position Nt836 in the cDNA sequence T-A resulting in the codon change TTT-TAT and the corresponding F to Y amino acid change)(see SEQ ID NO 4 for cDNA sequence, SEQ ID NO 5 for amino acid sequence and SEQ ID NO 2 for encompassing genomic sequence). In particular, GHR alleles characterized by the T to A (F279Y) substitution have been identified as being associated with an increased milk volume and altered milk composition in animals dependent upon whether they are homozygous with or without the substitution, or heterozygous carrying one substituted allele. More specifically, the presence of the F279Y amino acid change results in an increase milk yield and decrease milk fat and milk protein percentage as well as a decrease in live weight.

In addition a number of other nucleotide changes have been identified surrounding the F279Y polymorphic site (outlined in FIG. 3) that could be used either on there own or in combination to establish haplotypes corresponding to the F279Y allelic state.

The present invention thus relates to the use of the polymorphism (F279Y) and/or flanking polymorphisms in a method of identification and selection of a bovine having said polymorphisms as well as to providing markers specific for such identification. Kits comprising said markers for use in marker selection also form part of the present invention as do animals so selected.

In particular, the present invention is directed to a method of genotyping cows or bulls for the polymorphisms disclosed herein, selected cows or bulls so genotyped and milk, meat, embryos and semen from said selected cows and bulls respectively.

BRIEF DESCRIPTION OF THE DRAWINGS

The invention will now be described with reference to the Figures of the accompanying drawings in which:

FIG. 6: Shows a 104 bp nucleotide sequence of the bovine GHR gene and the DNA sequence change corresponding to the amino acid F279Y mutation associated with the QTL (SEQ ID NO 62). The primers used to amplify the region and position of the probes used to detect alleles are also shown (SEQ ID NOs 8, 9, 10, 11).

DETAILED DESCRIPTION OF THE PREFERRED EMBODIMENT

Figure 1:
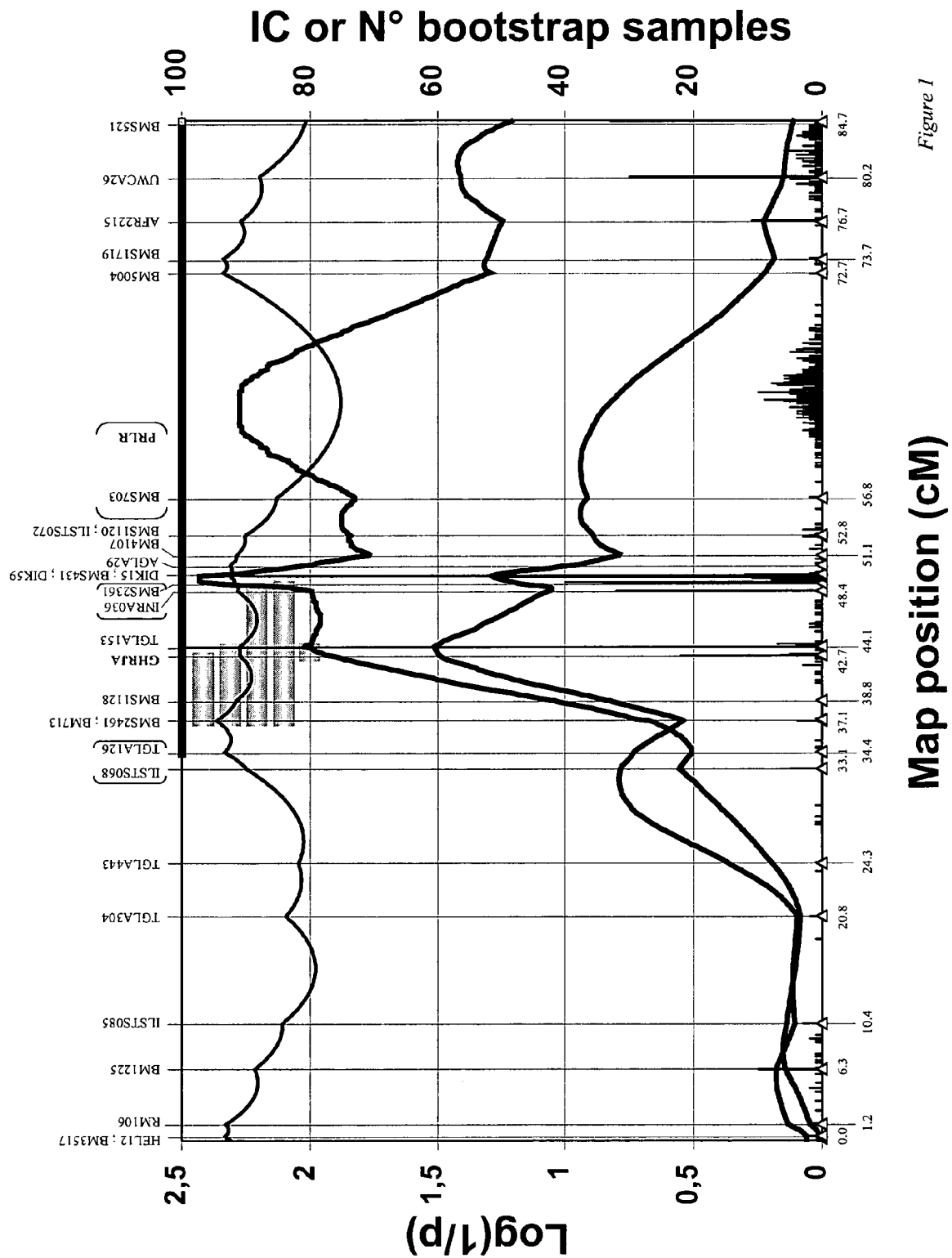
FIG. 1: A. Chromosome 20 microsatellite map. The name of the corresponding markers is given at the top of the figure and their respective position in centimorgan (Kosambi) at the bottom. GHRJA corresponds to a microsatellite marker in the promotor of the growth hormone receptor gene. The most likely position of the prolactin receptor (PRLR) inferred from the segregation of SNP markers (Sirja Moisio, in preparation) is given. Markers that could not be ordered with odds >1,000 are braced. The black curve running along the top quadrant of the chart correspond to the information content (expressed as a percentage—right Y-axis) obtained in the GDD. B. Conventional QTL mapping. The light and dark grey curves originating at the bottom left hand origin correspond to the location scores obtained respectively for milk protein % and milk fat %. Location scores are expressed as log(1/p) (left Y-axis) where p corresponds to the chromosome-wide probability to obtain the corresponding signal under the null hypothesis of no QTL determined by phenotype permutation. Most likely QTL positions obtained across 1,000 bootstrap samples (left Y-axis) are given as black vertical bars. The resulting 95% confidence interval is shown as a thick horizontal grey bar on the top axis of the figure. C. Haplotype-based test for association. Marker windows showing significant effects in the haplotype based association test are shown as light grey cylinders located at the top centre of the diagram. Their position with respect to the left Y-axis corresponds approximately to their significance level determined as described in M&M.

It has been discovered for the first time that the GHR gene in bovine is associated with the QTL, on chromosome 20 which is linked with improved milk and carcass production traits. More particularly, a novel polymorphism in the GHR gene has been discovered. It is thought that this polymorphism is responsible for these traits.

The method used for isolating genes which cause specific phenotypes is known as positional candidate cloning. It involves: (i) the chromosomal localisation of the gene which causes the specific phenotype using genetic markers in a linkage analysis; and (ii) the identification of the gene which causes the specific phenotype amongst the "candidate" genes known to be located in the corresponding region. Most of the time these candidate genes are selected from available mapping information in humans and mice.

The tools required to perform the initial localisation (step (i) above) are microsatellite marker maps, which are available for livestock species and are found in the public domain (Bishop et al., 1994; Barendse et al., 1994; Georges et al., 1995; and Kappes, 1997). The tools required for the positional candidate cloning, particularly the BAC libraries, (step (ii) above) are partially available from the public domain. Genomic libraries with large inserts constructed with Bacterial Artificial Chromosomes (BAC) are available in the public domain for most livestock species including cattle. For general principles of positional candidate cloning, see Collins, 1995 and Georges and Anderson, 1996.

Recently, a quantitative trait locus (QTL) which was shown to influence milk yield and composition, located on bovine chromosome 20, has been reported (Georges et al, 1995; Arranz et al, 1998). However, the exact location of the QTL on chromosome 20 was not known.

By using a denser chromosome 20 marker map and by exploiting linkage disequilibrium methods to refine the map position of the QTL the chromosome segment containing the gene coding for the growth hormone receptor was found to account for at least part of the chromosome 20 QTL effect.

This effect was further mapped to the nucleotide sequence of the GHR gene and a polymorphism associated with the chromosome 20 QTL shown to comprise a single base change at position Nt836 in the cDNA sequence T-A resulting in the codon change TTT-TAT and the corresponding amino acid substitution F279Y. Some of the genetic polymorphisms identified in the bovine GHR gene are reported in FIG. 3. The cDNA sequence is also set out as SEQ ID NO 4.

The sequence information in the Figures gives rise to numerous, and separate, aspects of the invention.

In one aspect, the invention provides a method of determining genetic merit of a bovine with respect to milk composition and volume, and/or live weight, which comprises the step of determining the bovine GHR genotypic state of said bovine. In particular, this method is useful for genotyping and selecting cows and bulls having the desired genotypic state so that milk, meat, embryos and semen may be collected from said cows and bulls respectively. Such semen would be useful for breeding purposes to produce bovine having the desired genotypic and, as a result, phenotypic state. In addition, cows genotyped by the methods of the present invention are also useful for breeding purposes, particularly for breeding with the selected bulls and/or to be artificially inseminated with the semen from selected bulls. The embiyos and offspring produced by such cows also form part of the present invention.

In one embodiment, the genotypic state is determined with respect to DNA obtained from said bovine.

Alternatively, said genotypic state is determined with reference to MRNA obtained from said bovine.

In yet a further embodiment, the genotypic state is determined with reference to the amino acid sequence of expressed bovine GHR protein obtained from said bovine.

Conveniently, in said method, the genotypic state of DNA encoding bovine GHR is determined, directly or indirectly.

Alternatively, in said method the genotypic state of at least one nucleotide difference from the nucleotide sequence encoding bovine GHR is determined, directly or indirectly.

More specifically, in said method the genotypic state of bovine GHR allele(s) characterised by the nucleotide substituition at position Nt836 on the cDNA sequence (SEQ ID NO 4) (TTT to TAT resulting in the corresponding F279Y amino acid substitution) is determined, directly or indirectly.

Figure 3:
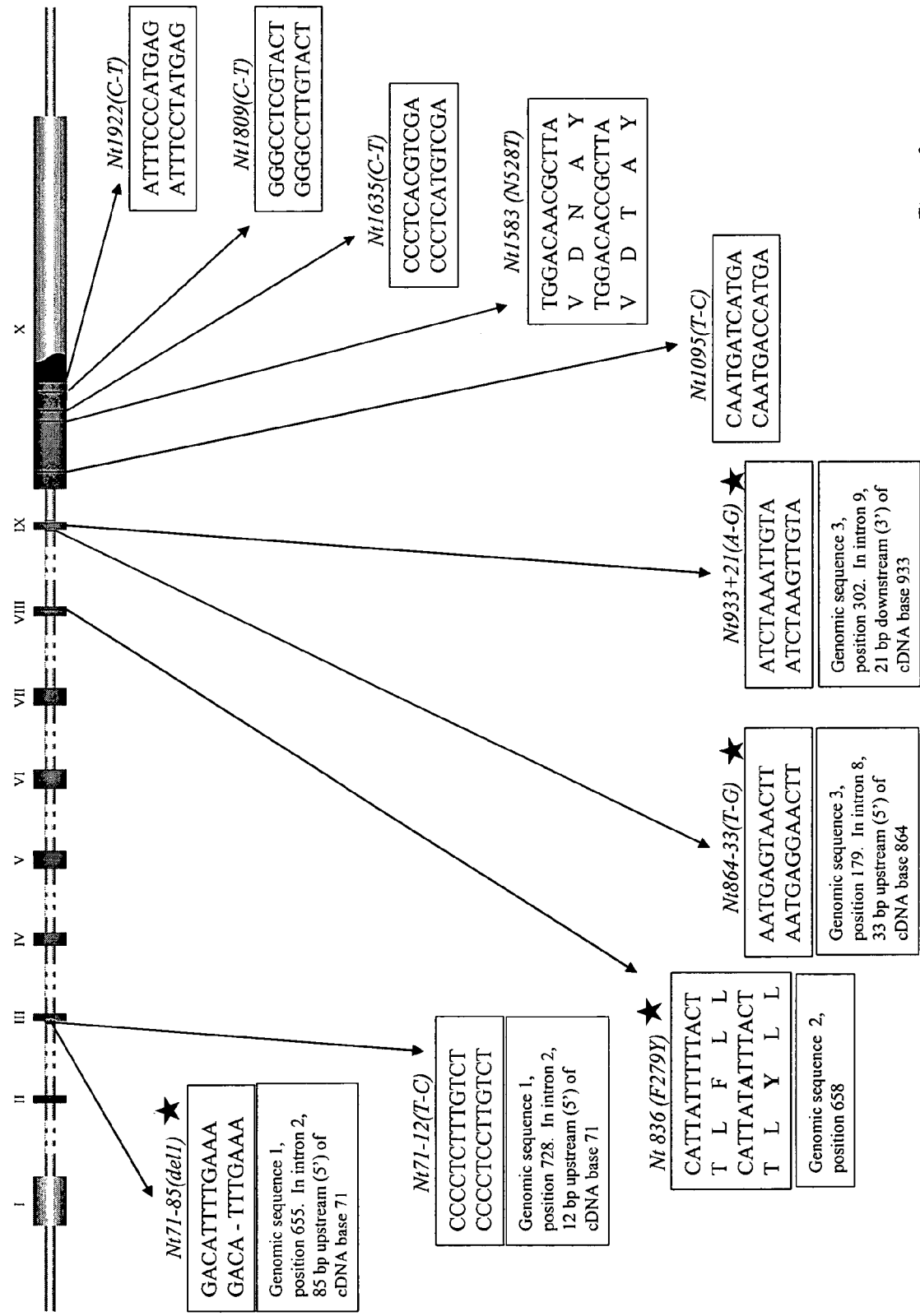
FIG. 3: Shows a schematic representation of the bovine GHR gene. The ten exons are shown as large cylinders and labelled by exon number. Coding sequences are shown in dark grey, 3' and 5' UTR sequences in light grey. Introns are shown as interrupted thin cylinders. SNPs are marked as lines connected with a box detailing the corresponding DNA sequences. The SNPs for which sires 1 and 18 were found to be hetereozygous are marked by asterisks. Refer to SEQ ID NOs 1, 2 and 3 for genomic sequence and SEQ ID NO 4 for cDNA sequence, and polymorphisms.

Alternately in said method the genotypic state of bovine GHR allele(s) characterised by the nucleotide substituitions described in FIG. 3 determined either directly or indirectly.

There are numerous art standard methods known for determining whether a particular DNA sequence is present in a sample. An example is the Polymerase Chain Reaction (PCR). A preferred aspect of the invention thus includes a step in which ascertaining whether the A to T substitution at position Nt836 in the sequence of GHR cDNA is present, includes amplifying the DNA in the presence of primers based on the nucleotide sequence of the GHR gene and flanking sequence, and/or in the presence of a primer containing at least a portion of a polymorphism as disclosed herein and which when present results in altered relative milk fat and protein production, and milk volume. The same technical approach can be undertaken to determine the genotypic state of any or all of the polymorphisms outlined in FIG. 3. The F279Y amino acid substitution polymorphism is used as an example in the following descriptions.

A primer of the present invention, used in PCR for example, is a nucleic acid molecule sufficiently complementary to the sequence on which it is based and of sufficient length to selectively hybridise to the corresponding portion of a nucleic acid molecule intended to be amplified and to prime synthesis thereof under in vitro conditions commonly used in PCR. Likewise, a probe of the present invention, is a molecule, for example a nucleic acid molecule of sufficient length and sufficiently complementary to the nucleic acid molecule of interest, which selectively binds under high or low stringency conditions with the nucleic acid sequence of interest for detection thereof in the presence of nucleic acid molecules having differing sequences. A marker of the present invention is a nucleic acid molecule corresponding to the GHR gene or a fragment or variant thereof or a flanking region useful for genotyping and/or selecting a bovine having one or more of the polymorphisms of the present invention. Single markers or a combination of markers, including a haplotype marker set (ie a haplotype being a group of markers used to determine the genotypic state across a region of DNA or an allele, especially with reference to the state of the F279Y polymorphism) may be used to genotype and/or select bovine according to the present invention.

In another aspect, the invention provides a method for determining the genetic merit of bovine with respect to milk content and volume with reference to a sample of material containing MRNA obtained from the bovine. This method includes ascertaining whether the T to A substitution in the sequence of the mRNA encoding GHR is present. The presence of such a substitution again indicates an association with altered relative milk volume and composition.

Again, if an amplification method such as PCR is used in ascertaining whether the polymorphism in the sequence of the mRNA encoding GHR is present, the method includes reverse transcribing the mRNA using a reverse transcriptase to generate a cDNA and then amplifying the cDNA in the presence of a pair of primers complementary to a nucleotide sequence encoding a protein having biological activity of wild type GHR.

In a further aspect, the invention includes the use of a probe in the methods of genotyping according to the invention wherein the probe is selected from any 5 or more contiguous nucleotides of the GHR sequence as shown in FIG. 6, which is therefore sufficiently complementary with a nucleic acid sequence encoding such bovine GHR, or its complement, so as to bind thereto under stringent conditions. Diagnostic kits containing such a probe are also included. Such probes may be selected from:

```
Adara1:  CAGTGACATTATATTTACTC;

and

Adara2:  CAGTGACATTATTTTTACTC. (SEQ ID NOs: 10 and 11 respectively)
```

The invention further includes an isolated nucleic acid molecule comprising a DNA molecule having in whole or in part the nucleotide sequence identified in FIG. 6 (SEQ ID NO: 62) or which varies from the sequence due to the degeneracy of the genetic code, or a nucleic acid strand capable of hybridising with said nucleic acid molecule under stringent hybridisation conditions.

The invention includes isolated mRNA transcribed from DNA having a sequence which corresponds to a nucleic acid molecule of the invention.

The invention also includes a primer composition useful for detection of the presence of DNA encoding GHR and/or the presence of DNA encoding a variant protein. In one form, the composition can include a nucleic acid primer substantially complementary to a nucleic acid sequence encoding GHR. The nucleic acid sequence can in whole or in part be that identified in FIG. 6 (SEQ ID NO: 62). Diagnostic kits including such a composition are also included.

The invention further provides a diagnostic kit useful in detecting DNA encoding a variant GHR protein in bovine which includes first and second primers for amplifying the DNA, the primers being complementary to nucleotide sequences of the DNA upstream and downstream, respectively, of a polymorphism in the portion of the DNA encoding GHR which results in altered milk volume and composition. The kit can also include other primers complementary to either the T or A variants, located on the GHR gene.

The development of allele specific antibodies designed to detect the presence of either the F or Y at position 279 of the GHR gene is also contemplated. Methods of preparing such antibodies are well known in the art. Such allele specific antibodies may then be used in a method for the selection of bovine animals. Specifically, a diagnostic kit it contemplated containing such antibodies and means for detecting the antibody when bound to DNA. The diagnostic kit can also contain an instruction manual for use of the kit.

Antibody-based diagnostics are of course not the only possibility. A further diagnostic kit may comprise a nucleotide probe complementary to the sequence, or an oligonucleotide fragment thereof, shown in FIG. 6, for example, for hybridisation with mRNA from a sample of cells; means for detecting the nucleotide probe bound to mRNA in the sample with a standard. In a particular aspect, the kit of this aspect of the invention includes a probe having a nucleic acid molecule sufficiently complementary with a sequence identified in FIG. 6, or its complement, so as to bind thereto under stringent conditions. "Stringent hybridisation conditions" takes on its common meaning to a person skilled in the art. Appropriate stringency conditions which promote nucleic acid hybridisation, for example, 6× sodium chloride/sodium citrate (SSC) at about 45° C. are known to those skilled in the art, including in Current Protocols in Molecular Biology, John Wiley & Sons, NY (1989). Appropriate wash stringency depends on degree of homology and length of probe. If homology is 100%, a high temperature (65° C. to 75° C.) may be used. If homology is low, lower wash temperatures must be used. However, if the probe is very short (<100 bp), lower temperatures must be used even with 100% homology. In general, one starts washing at low temperatures (37° C. to 40° C.), and raises the temperature by 3-5° C. intervals until background is low enough not to be a major factor in autoradiography. The diagnostic kit can also contain an instruction manual for use of the kit.

One of the major applications of the present invention is in the marker assisted selection of bovines having a polymorphism in the GHR gene and which are associated with improved milk production traits. The invention therefore provides a diagnostic kit which can be used to determine the GHR genotype of bovine genetic material, for example. One kit includes a set of primers used for amplifying the genetic material. A kit can contain a primer including a nucleotide sequence for amplifying a region of the genetic material containing the T to A polymorphism coding for the F279Y amino acid change described herein. Such a kit could also include a primer for amplifying the corresponding region of the normal GHR gene, i.e. the sequence without the polymorphism. Usually, such a kit would also include another primer upstream or downstream of the region of interest complementary to a coding and/or non-coding portion of the gene. These primers are used to amplify the segment containing the mutation, i.e. polymorphism, of interest.

In particular, the invention is directed to the use of the polymorphism in the GHR gene in the genotyping of cows and bulls as well as to cows and bulls selected by such genotyping which has identified the variation present in the GHR gene. Such bulls so selected are of valuable breeding stock and the invention is also directed to the semen produced by such selected bulls for breeding purposes. Cows so selected are also useful as breeding stock as are their offspring. In addition, such cows may produce valuable dairy herds as the milk produced by such cows is produced in greater volumes than equivalent non-selected cows, and/or has an altered composition in that it comprises lower milkfat percentage and lower milk protein percentage corresponding to the inheritance of tyrosine at position 279 in the GHR protein.

Thus, the present invention involves genotyping bovine, both cows and bulls, for the T to A variation disclosed herein, selected cows and bulls so genotyped, milk and semen produced by the selected cows and bulls so genotyped, offspring produced by the selected bovine, including embryos and cells (including cell lines) useful for cloning said selected bovine.

The actual genotyping is carried out using primers that target specific polymorphisms as described herein and that could function as allele-specific oligonucleotides in conventional hybridisation, Taqman assays, OLA assays, etc. Alternatively, primers can be designed to permit genotyping by microsequencing.

These are but a selection of the applications of this invention. Others will be apparent to those persons skilled in this art and are in no way excluded. To the contrary, the invention extends to cover not only the specific teaching provided but also all variations and modifications which are within the skill and contemplation of the addressee.

The invention will now be defined by specific examples which are illustrative only and are not intended to limit the invention in any way.

EXPERIMENTAL

1. Materials & Methods

Pedigree Material

The pedigree material used in this study comprised:

Data set I: a previously described Black-and-White Holstein-Friesian grand-daughter design sampled in the Netherlands and composed of 22 paternal half-sib families for a total of 987 bulls (Spelman et al., 1996; Coppieters et al., 1998a);

Data set II: 276 progeny-tested Holstein-Friesian sires sampled in the Netherlands;

Data set III: 1550 progeny-tested Holstein-Friesian sires sampled in New Zealand.

Data set IV: 959 progeny-tested Jersey sires sampled in New Zealand

Data set V: 485 Holstein-Friesian cows sampled in New Zealand.

Data set VI: 387 Jersey cows sampled in New Zealand.

Phenotypes

Phenotypes were respectively daughter yield deviations (DYD) for bulls, lactation values (LV=unregressed first lactation yield deviations) for cows, as well as average parental predicted transmitting abilities (PTA) for bulls and cows for milk protein and fat yield, as well as protein and fat percentage (Van Raden & Wiggans, 1991). DYDs, lactation values and PTA were directly obtained from CR-DELTA (Netherlands)(Data sets I and II) or LIC (New Zealand)(Data sets III-VI) respectively.

Map Construction

Microsatellite genotyping, map construction and information content mapping were performed as previously described (Coppieters et al., 1998a). Sequence information for the primers used for PCR amplification of anonymous Type II microsatellite markers can be obtained from ArkDB (WorldWideWeb at thearkdb.org/species.html). The following primers were designed based on Heap et al. (1995) to amplify a microsatellite in the promotor region of the growth hormone receptor gene: GHRJA.UP: 5'-TGCTCTAATCTTTTCTGGTACCAGG-3' and GHR-JA.DN: 5'-TCCTCCCCAAATCAATTACATTTTCTC-3' (SEQ ID NOS: 60 and 61 respectively).

Conventional QTL Mapping

QTL mapping was performed by multimarker regression (Knott et al., 1996) using the previously described HSQM software (Coppieters et al., 1998b). Chromosome-wide significance thresholds were determined by permutation as previously described (Churchill & Doerge, 1995; Coppieters et al., 1998b). Segregating sire families were identified based on the results of within-family analyses as previously described (Coppieters et al., 1998a).

Haplotype Based Test for Association.

Assumptions. It was assumed that a QTL is characterized by two additively acting alleles, "Q" and "q", that segregate in the population of interest with respective allelic frequencies of q and (1-q). It was also assumed that the "Q" allele appears in the population by mutation or migration on a chromosome with haplotype "H" for a series of flanking markers. All other haplotypes were pooled and referred to as "O". At the present generation the "H" haplotype may still be in LD with the "Q" allele by an amount D. The "H" to "O" haplotype substitution effect can then be shown to equal:

$$\alpha = a \frac{D}{h(1-h)}$$

where a corresponds to half the difference between the phenotypic values of "QQ" versus "qq" individuals, and h corresponds to the population frequency of the "H" haplotype (Falconer & Mackay, 1996).

Test for association. Knowing that in the present GDD, phased marker genotypes were available for all sons, their sires but NOT their dams as these were not marker genotyped, and defining $T_i$ as $[DYD_i - PA_i]$, where $DYD_i$ was the daughter yield deviation of son i and $PA_i$ was the average predicted transmitting ability (Van Raden and Wiggans, 1991) of the sire and dam of son i, the expected value of $T_i$ can be expressed as a function of the marker genotype of the sire's chromosomes (SC), and the marker genotypes of the paternal (PC) and maternal gametes (MC) inherited by son i, as shown in Table 1 below:

TABLE 1

Expected values of T (=DYD − PA) as a function of the marker genotype of the sire, and the marker genotypes of the paternal and maternal gametes inherited by the son.

| Paternal genotype (SC) | Paternal gamete (PC) | Maternal gamete (MC) | |
|---|---|---|---|
| | | H | O |
| HH | H | $T = 1/2\alpha h$ | $T = -1/2\alpha(1-h)$ |
| HO | H | $T = 1/2\alpha(1+h)$ | $T = 1/2\alpha h$ |
| | O | $T = -1/2\alpha(1-h)$ | $T = -1/2\alpha(2-h)$ |
| OO | O | $T = 1/2\alpha h$ | $T = -1/2\alpha(1-h)$ |

SC, PC, MC, H, O, α and h are as defined in Materials & Methods

Expected values of $T_i$ were seen to be linear functions of the unknown haplotype substitution effect, α. A least square estimator of α was therefore easily obtained by linear regression, while the ratio:

$$\frac{SSR}{SSE/(n-2)}$$

which is distributed as an F statistic with 1 and n-2 degrees of freedom, was used to measure the evidence in favour of a statistically significant haplotype substitution effect. n corresponds to the number of sons available in the GDD.

By using $T_i$ as phenotype, one was essentially performing a transmission disequilibrium test (TDT, Spielman et al., 1993) which simultaneously tested for association and linkage. As the dams were not genotyped, however, the TDT reduced in part to a conventional association test.

Choice of markers and haplotypes. So far, the applicants have not defined which of the m markers available on the chromosome have to be considered when defining a haplotype. As the exact location of the QTL is not known, nor the size of the haplotype that will maximize α, all possible windows comprising between one and m adjacent markers were tested separately. The applicants thus examined m windows of one marker, (m-1) windows of two markers, (m-2) windows of three markers, . . . , and one window of m markers.

Having selected the markers composing the haplotype, it was necessary to chose the "H" haplotype amongst all haplotypes encountered in the population. In the proposed approach, the haplotypes that were successively considered as "H" haplotypes corresponded to the chromosomes of the "s" sires in the GDD that were known to be heterozygous "Qq" for the QTL based on the results of a marker assisted segregation analysis performed in their sons (see above). As it was not known, a priori, which of the sire's homologues carried the "Q" allele, the haplotypes corresponding to both chromosomes were examined, for a total of 2s homologues.

When estimating the substitution effect of the haplotypes of a given sire, its sons were eliminated from the data set, in order to avoid extracting information that would be redundant with the linkage analysis.

Significance thresholds. The F-ratio defined above does not account for the multiple tests that were performed, i.e. the $(m^2+m)/2$ marker windows tested for each of the 2s homologues. The applicant accounted for multiple testing by applying a permutation test. The phenotypes and marker genotypes were shuffled 1,000 times and the $2s(m^2+m)/2$ tests performed on each permutated data set. The highest F-ratios obtained with the real data were then compared with the highest F-ratios obtained across the 1,000 permutations.

Simultaneous Mining of Linkage and Linkage Disequilibrium

QTL fine-mapping exploiting both linkage and LD. The utilized mapping method was implemented in the LDVCM (LD variance component mapping) programs, and can be summarized as follows. To test for the presence of a QTL at map position p of the studied chromosome:

1. For all markers on the studied chromosome, the applicant determined the marker linkage phase of the sires and sons as described (Farnir et al., 2002). As a consequence, the marker data then consisted of 2s sire chromosomes (SC), n paternally inherited chromosomes of the sons (PC), and n maternally inherited chromosomes of the sons (MC), where s and n corresponded respectively to the number of sire families and the number of sons in the GDD. From the genotypes of the PC, the probability that son i inherited the "left" ($\lambda_p$) or "right" ($\rho_p = 1 - \lambda_p$) SC from its sire at map position p was easily computed as described (Coppieters et al., 1998b).

2. The applicant computed identity-by-descent (IBD) probabilities ($\phi_p$) for all pair wise combinations of SC and MC using the method described by Meuwissen & Goddard (2001). This method approximates the probability that two chromosomes are IBD at a given map position conditional on the identity-by-state (IBS) status of flanking markers, on the basis of coalescent theory (Hudson, 1985). Windows of sixteen markers were considered to compute $\phi_p$.

3. Using $(1-\phi_p)$ as a distance measure, the applicant applied the UPGMA hierarchical clustering algorithm (e.g. Mount, 2001) to generate a rooted dendrogram representing the genetic relationship—at position p—between all SC and MC haplotypes encountered in the population.

4. The applicant used the logical framework provided by this dendrogram to group the SC and MC in functionally distinct clusters. A cluster is defined as a group of haplotypes that coalesce into a common node. A useful feature of UPGMA trees in this regard is that the distance $(1-\phi_p)$ between all the haplotypes that coalesce into a given node is $\leq 2\times$ the distance between the node and any of these haplotypes. As a consequence, the tree is scanned downwards from the root and branches are cut until nodes are reached such that all coalescing haplotypes (i.e. all haplotypes within the cluster) have a distance measure $(1-\phi_p)<T$ (Kim et al., 2002).

5. The applicant modelled the sons' phenotypes (DYDs) using the following linear model:

$$y = Xb + Z_h h + Z_u u + e$$

wherein y is the vector of phenotype records of all sons. b is a vector of fixed effects which in this study reduces to the overall mean. X is incidence matrix relating fixed effects to individual sons, which in this study reduces to a vector of ones. h is the vector of random QTL effects corresponding to the defined haplotype clusters. $Z_h$ is an incidence matrix relating haplotype clusters to individual sons. In $Z_h$, a maximum of three elements per line can have non-zero value: "1" in the column corresponding to the cluster to which the MC haplotype belongs, "$\lambda_p$" and "$\rho_p$" in the columns corresponding respectively to the haplotype clusters of the "right" and "left" SC. If either of the SC and/or MC belong to the same cluster, the corresponding coefficients are added. u is the vector of random individual polygenic effects ("animal model": Lynch and Walsh, 1997). $Z_u$ is a diagonal incidence matrix relating individual polygenic effects to individual sons. e is the vector of individual error terms.

Haplotype cluster effects with corresponding variance, $\sigma_H^2$, individual polygenic effects with corresponding variance, $\sigma_A^2$, and individual error terms with corresponding variance, $\sigma_E^2$, were estimated using AIREML (Johnson and Thompson, 1995), by maximizing the restricted log likelihood function L:

$$L = 0.5 ln|V| - 0.5 ln|X^T V^{-1} X| - 0.5(y - X\hat{b})^T V^{-1}(y - X\hat{b})$$

In this, V equals:

$$V = \sigma_H^2 Z_h H Z_h^T + \sigma_A^2 Z_u A Z_u^T + \sigma_E^2 I$$

Because the applicant assumed that the covariance between the QTL effects of the different haplotype clusters is zero, H reduces to an identity matrix. This differentiates the present approach from that of Meuwissen and Goddard (2000), in which H is the matrix of between haplotype IBD probabilities. A is the additive genetic relationship matrix (Lynch and Walsh, 1997).

6. Steps 4 and 5 were repeated for all possible values of T (from 0 to 1), in order to identify a restricted maximum likelihood (REML) solution for map position p. By analogy with Famir et al. (2002) the applicant denoted the hypothesis corresponding to this REML solution as $H_2$.

QTL mapping exploiting linkage only. Note that the previous model could be extended with minor modifications to map QTL by exploiting linkage information only. This was simply achieved by ignoring all MCs and considering that all SCs belong to distinct haplotype clusters, irrespective of their marker genotype. REML solutions for the different parameters was found as described in the previous section. Again by analogy with Farnir et al. (2002), the corresponding hypothesis was referred to as H1.

Hypothesis testing and significance thresholds. The log likelihood of the data under the $H_2$ and $H_1$ hypotheses were compared with that under the null hypothesis, $H_0$, of no QTL at map position p. The latter was computed as described above but using the reduced model:

$$Y = Xb + Z_u u + e$$

Evidence in favor of a QTL at map position, p, was then expressed as a lod score:

$$z_p = 0.43 * (L_{H_{1/2}} - L_{H_0})$$

As customary when performing interval mapping, the applicant was sliding the hypothetical position of the QTL throughout the chromosome map, and computing lod scores at each map position as described to generate chromosome-wide lod score profiles.

Kim et al. (2002) have shown by simulation that when analyzing a chromosome of 100 cM with a marker density of one marker every 5 cM, $2*\ln(10)*z_p$ has (under the null hypothesis) an approximate chi-squared distribution with two degrees of freedom corrected (Bonferroni correction) for two and six independent traits when testing respectively $H_1$ and $H_2$. Chromosome-wide significance levels were computed from these distributions in this study.

Sequencing the Coding Portion of the Growth Hormone Receptor (GHR) from Genomic DNA To develop primers that would allow the applicant to conveniently amplify and sequence the entire GHR coding sequence from bovine genomic DNA, a bovine BAC library (Warren et al., 2000) was screened using standard procedures with an oligonucleotide probe complementary to exon 10 and isolated eight GHR containing clones. DNA from one of these clones was used as template for sequencing the intron-exon boundaries using exonic primers designed based on the bovine cDNA sequence (e.g. Hauser et al., 1990) and predicted to flank exon-intron boundaries assuming conservation of intron position between human and cattle (e.g. Godowski et al., 1989). Based on the obtained intronic information primers were then designed to amplify and sequence most of the GHR coding sequence from genomic DNA using standard procedures. A list of such primers is set out in Table 2, below. Sequence traces were analyzed with the POLY-PHRED software (Nickerson et al., 1997).

TABLE 2

Primers used for amplification and sequencing of the GHR exons from bovine genomic DNA.

| | | |
|---|---|---|
| GHRex3_F | TAG GAG TTC CTT TTA GAG GAT AGG TGC | SEQ ID NO: 40 |
| GHRex3_R | GCC TTG TGG AGA AGT TGA CAA A | SEQ ID NO: 41 |
| GHRex4_F | GCC CAG AGA AAC AGC ATT TCT A | SEQ ID NO: 42 |

TABLE 2-continued

Primers used for amplification and sequencing of the GHR exons from bovine genomic DNA.

| | | |
|---|---|---|
| GHRex4_R | TCA CTG CCA TAT TTC CAG CAT C | SEQ ID NO: 43 |
| GHRex5_F | CTT GCT CAT AAA ATA CTC GTG TCC T | SEQ ID NO: 44 |
| GHRex5_R | ATG CAA TGG CAA AGT CTT CCT AC | SEQ ID NO: 45 |
| GHRex6_F | TGT ATG AAG TAA CTT AGT CGT CTT CG | SEQ ID NO: 46 |
| GHRex6_R | GAG AGG GGT TGT TGA ACA CAA A | SEQ ID NO: 47 |
| GHRex7_F | TCC TAC TTT CCA GAA ATT CAT TTT G | SEQ ID NO: 48 |
| GHRex7_R | CTG AGG CTA ATG TAT ATT GAT CTG GAC | SEQ ID NO: 49 |
| GHRex8_F | GTG GCT ATC AAG TGA AAT CAT TGA C | SEQ ID NO: 50 |
| GHRex8_R | ACT GGG TTG ATG AAA CAC TTC ACT C | SEQ ID NO: 51 |
| GHRex9_F | GCC TCA TCA TTC ACT GCT TA | SEQ ID NO: 52 |
| GHRex9_R | GGT TTC AAC ATA AGG CTC TG | SEQ ID NO: 53 |
| GHRex10_F | ACA TGG TTT GTT ATA TGA TTT TGT TAC | SEQ ID NO: 54 |
| GHRex10_R | TTC ATA TTC CCC ACC CTC AAC T | SEQ ID NO: 55 |
| GHRex10_1F | ACA TTC TGG AGG CTG ATT TC | SEQ ID NO: 56 |
| GHRex10_2F | CAA AAG AAT AAG ACT GGG AA | SEQ ID NO: 57 |
| GHRex10_1R | AGC TTG GCT CTA CGT GTG AT | SEQ ID NO: 58 |
| GHRex10_2R | GAT AAC ACT GGG CTG CTG GT | SEQ ID NO: 59 |

All primer sequences are written 5'->3'. All exons were PCR amplified and sequenced with the same primers except for exon 10 which was amplified with GHRex10_F and GHRex10_R then sequenced with these primers plus GHRex10__1F, GHRex10_R, GHRex10__2F and GHRex10__2R.

Oligonucleotide Ligation Assay (OLA)

An OLA test to genotype the GHR polymorphism encoding the F279Y amino acid change (following on is a description of a TaqMan assay also used), Nt864–33(T-G), Nt933+21(A-G), Nt1095(T-C), N528T (Nt1583) and Nt1922(C-T) SNPs in multiplex was developed as previously described (Karim et al., 2000). The primers used for the PCR amplification step and the ligation reaction are reported in Table 3 below:

TABLE 3

Primers (5'-3') used for OLA multiplexing of GHR SNPs

| | PCR | | OLA | | |
|---|---|---|---|---|---|
| SNP | UP | DN | AS1 | AS2 | C |
| F279Y | 1UP | 1DN | 1AS1 | 1AS2 | 1C (SEQ ID NO: 14) |
| | (SEQ ID NO: 6) | (SEQ ID NO: 7) | (SEQ ID NO: 12) | (SEQ ID NO: 13) | P- |
| | GTGGCTATCAAGT | ACTGGGTTGATGAAAC | Fam- | Hex- | TTTACTCATATTTTCTA |

TABLE 3-continued

Primers (5'-3') used for OLA multiplexing of GHR SNPs

| | PCR | | OLA | | |
|---|---|---|---|---|---|
| SNP | UP | DN | AS1 | AS2 | C |
| | GAAATCATTGAC | ACTTCACTC | GGGCTAGCAGTGACAT | GGGCTAGCAGTGACAT | AACAGC |
| | | | TATA | TATT | |
| Nt864 − 33(T-G) | 2UP | 2DN | 2AS1 | 2AS2 | 2C (SEQ ID NO: 19) |
| | (SEQ ID NO: 15) | (SEQ ID NO: 16) | (SEQ ID NO: 17) | (SEQ ID NO: 18) | P- |
| | GCCTCATCATTCA | GGTTTCAACATAAGGC | Fam- | Hex- | AACTTACATCAAAACA |
| | CTGCTTA | TCTG | GTCTTTTGAAATGAGA | GTCTTTTGAAATGAGA | AAATTTTG |
| | | | TGAGG | ATGAGT | |
| Nt933 + 21(A-G) | 3UP | 3DN | 3AS1 | 3AS2 | 3C (SEQ ID NO: 24) |
| | (SEQ ID NO: 20) | (SEQ ID NO: 21) | (SEQ ID NO: 22) | (SEQ ID NO:23) | P- |
| | GCCTCATCATTCA | GGTTTCAACATAAGGC | Fam- | Hex- | TTGTACATGACACTAA |
| | CTGCTTA | TCTG | CAAGGTAATTAATAAA | CAAGGTAATTAATAAA | TTAAATGT |
| | | | ATATCTAAG | ATATCTAAA | |
| Nt1095(T-C) | 4UP | 4DN | 4AS1 | 4AS2 | 4C (SEQ ID NO: 29) |
| | (SEQ ID NO: 25) | (SEQ ID NO: 26) | (SEQ ID NO: 27) | (SEQ ID NO: 28) | P- |
| | TCTTGGGTTGAAT | ATCGCACATGTCACTG | Fam- | Hex- | CATGAAAAATCACTCA |
| | TTATTGAACTAG | ACATGGAA | CAGACTTCTGAGCAAT | CAGACTTCTGAGCAAT | ATATC |
| | | | GAC | GAT | |
| N528T(Nt1583) | 5UP | 5DN | 5AS1 | 5AS2 | 5C (SEQ ID NO: 34) |
| | (SEQ ID NO: 30) | (SEQ ID NO: 31) | (SEQ ID NO: 32) | (SEQ ID NO: 33) | P- |
| | ACATTACACCAGC | TGGTAAGGCTTTCTGTG | Fam- | Hex- | CGCTTACTTCTGCGAG |
| | AGGAAATGTGGT | GTGATGT | TAACTTCATCGTGGAC | TAACTTCATCGTGGAC | |
| | | | AC | A | |
| Nt1922(C-T) | 6UP | 6DN | 6AS1 | 6AS2 | 6C (SEQ ID NO: 39) |
| | (SEQ ID NO: 35) | (SEQ ID NO: 36) | (SEQ ID NO: 37) | (SEQ ID NO: 38) | P- |
| | AGGTCGGGGAC | TCATATTCCCCACCC | Fam- | Hex- | ATGAGCTACCCATTG |
| | AGCAGAACAT | TCAACTCA | AGCTTTTCTTTGATT | AGCTTTTCTTTGATT | AAT |
| | | | TCCC | TCCT | |

Detecting the Allelic Variants Causing the F279Y Amino Acid Change

The F279Y variation (T to A) was also detected using a TaqMan assay as follows:

Primer Sequences 5' to 3':

```
AdaraforAD primer:
CCAGTTTCCATGGTTCTTAATTATTATCTT    (SEQ ID NO: 8)

AdararevAD primer:
GGTTATATCACACTTACCTTTGCTGTTTAG    (SEQ ID NO: 9)
```

Probe Sequences 5' to 3':

```
Adara1:
CAGTGACATTATATTTACTC              (SEQ ID NO: 10)

Adara2:
CAGTGACATTATTTTTACTC              (SEQ ID NO: 11)
```

Both probes use MGB (minor groove binder) as a non-fluorescent quencher.

The final reaction conditions are 1× Universal PCR Mastermix (Applied Biosystems), 500 nM each primer (Invitrogen), 100 nM Adara1 (FAM) probe, 200 nM Adara2 (VIC) probe (Applied Biosystems) and 2 µl of a 1/20 dilution of DNA template in a total volume of 10 µl.

Cycling conditions were 50° C. for 2 minutes, 95° C. initial denaturation for 10 minutes, then 40 cycles of denaturation at 94° C. for 15 seconds, annealing and extension 60° C. for 1 minute.

```
ADARAFORAD      CCAGTTTCCATGGTTCTTAATTATTATCTT      →
                CCAGTTTCCATGGTTCTTAATTATTATCTTTGGAATACTTGGGCTAGCAG

TGACATTAT TTTACTCATATTTTCTAAACAGCAAAGGTAAGTGTGATATAACC
                ←  GATTTGTCGTTTCCATTCACACTATATTGG  ADARAREVAD
```

(SEQ ID NO 62)

The probe positions are underlined. The polymorphic site is highlighted and is either an A or T. This is at position 836 of the coding region with numbering starting at the ATG start site.

A 104 bp product was produced in this reaction. When the A allele was present the FAM-labelled probe bound and fluoresced at 518 nm. When the T allele was present the VIC-labelled probe bound and fluoresced at 554 nm. After cycling was complete, the plate was scanned on the ABI7900 Sequence Detection System, and the fluorescence from each well detected. The resulting scattergraph separated out into 3 clumps with A homozygotes (phenylalanine) in the upper left hand corner, T homozygotes (tyrosine) in the lower right hand corner and TA heterozygotes in between. Each clump was circled and the software automatically determined the genotype for each sample. On each plate there were controls with 8 wells each of known homozygotes, heterzygotes and no template controls.

Estimating the Effect on Milk Yield and Composition Associated with the F279Y Polymorphism in the General Dairy Cattle Population The effect of the genotypic variation on milk yield and composition was estimated using the model:

$$y_i = \mu + g_i + a_i + e_i$$

where $y_i$ were DYDs when studying bulls or lactation values when studying cows, $g_i$ is a fixed effect corresponding to the genotypic variation (TT, AA or TA), $a_i$ is a random polygenic component accounting for all known pedigree relationships ("animal model" (Lynch and Walsh 1997) including ungenotyped individuals whose phenotypes were ignored) and $e_i$ is a random residual. Maximum likelihood solutions for $g_i$, $a_i$, $e_i$, were obtained using the MTDFREML program (Boldman et al. 1993), setting $\sigma_a^2/(\sigma_a^2+\sigma_e^2)$ for yield (percentage) traits at 70% (75%) and 35% (50%) for DYDs and LVs respectively.

The statistical significance of the T to A genotype effect was estimated from:

$$\frac{3*(SSM_F - SSM_R)}{(n-3)*SSE_F}$$

where $SSM_F$, $SSM_R$ and $SSE_F$ are the sum of squares due to the full model, reduced model and error (full model) respectively, which is distributed as an F-statistic with 3 and (n-3) degrees of freedom.

2. Results

Construction of a High Density Microsatellite Map of Bovine Chromosome 20

In order to refine the map position of the chromosome 20 QTL, the marker density on this chromosome was first increased. Data set I for 22 additional, publicly available microsatellites known to map to bovine chromosome 20 as well as for a microsatellite in the promotor region of the bovine growth hormone receptor gene (GHRJA) was genotyped. A male linkage map was constructed comprising 29 markers covering 85 cM(K) with average marker interval of 3 cM(K). The information content of the corresponding map was computed as previously described (Coppieters et al., 1998a). It was superior to 80% for most of the chromosome length. The map, shown in FIG. 1, also reports the position of the prolactin receptor gene (PRLR) deduced from segregation data of prolactin receptor SNPs in the same pedigree material (Sirja Moisio, unpublished observations). Note that in the human, the GHR gene is located in band 5p13.3 at map position 37.4 Mb on the "golden path" human sequence (Ensembl Human Genome Server: WorldWideWeb at ensembl.org), while the PRLR gene is located in band 5p13.1 at map position 50.9 Mb, i.e. at approximately 15 Mb from the former. The genetic distance separating the bovine GHR and PRLR genes are therefore compatible with the human data.

Conventional QTL Mapping Using a Dense Marker Map

These novel microsatellite genotypes were then used to repeat a QTL mapping analysis in data set I. FIG. 1 reports the location scores that were obtained by multimarker regression in the across-family analysis along the newly generated chromosome 20 marker map. As expected, these results confirm the presence of a QTL with strong effect on protein percentage at most likely position 49 cM. The QTL affected fat percentage to a lesser extent and had only very modest influence on the yield traits (data not shown).

Bootstrap analyses were performed for protein percentage according to Visscher et al. (1996) to estimate the 95% confidence interval (CI) for the position of the QTL. FIG. 1 illustrates the distribution of the most likely position of the QTL across 1,000 bootstrap samples as well as the deduced 95% CI. It can be seen that the CI covers approximately 50 cM which in essence corresponds to the distal half of chromosome 20 and therefore to a very poor location of the QTL.

Within-family regression analyses was then performed on protein percentage as described (Arranz et al., 1998) to identify sire families that were segregating for this QTL. Two such families were identified in data set I: families 1 and 18 (data not shown).

Refining the Map Position of a QTL: Use of a Haplotype Based Test for Association.

The previously described within family analyses indicate that sires 1 and 18 were heterozygous for QTL alleles with large substitution effects ("Q") on chromosome 20. Previous work within the same population revealed extensive genome wide linkage disequilibrium due to random drift (Famir et al., 2000). It was therefore hypothesized that the marker haplotypes flanking the "Q" alleles in the segregating sires might well be in linkage disequilibrium with the same "Q" alleles in the general population as well. To test this hypothesis, we measured the effect on protein percentage of the sire haplotypes in the general population using the haplotype based test for association described in Materials & Methods above.

By doing so, five haplotype windows were identified that yielded significant F-ratios (p<0.01 after correction for multiple testing) corresponding to substitution effects of ≈0.03% milk protein. The corresponding haplotypes were all derived from a chromosome segment that was shared identical-by-descent by sires 1 and 18. The sons of both sires were eliminated from the data set prior to performing the test for association. FIG. 1 shows the position and statistical significance of the corresponding marker windows. It can be seen that their position centers around the TGLA153-GHRJ marker pair, corresponding to a minor peak for protein %, but the most likely QTL position when analyzing fat %. This result strongly suggests that a gene in the vicinity of these markers indeed contributes to the QTL effect observed on bovine chromosome 20.

Refining the Map Position of a QTL: Combined Linkage and LD Analysis.

Figure 2:
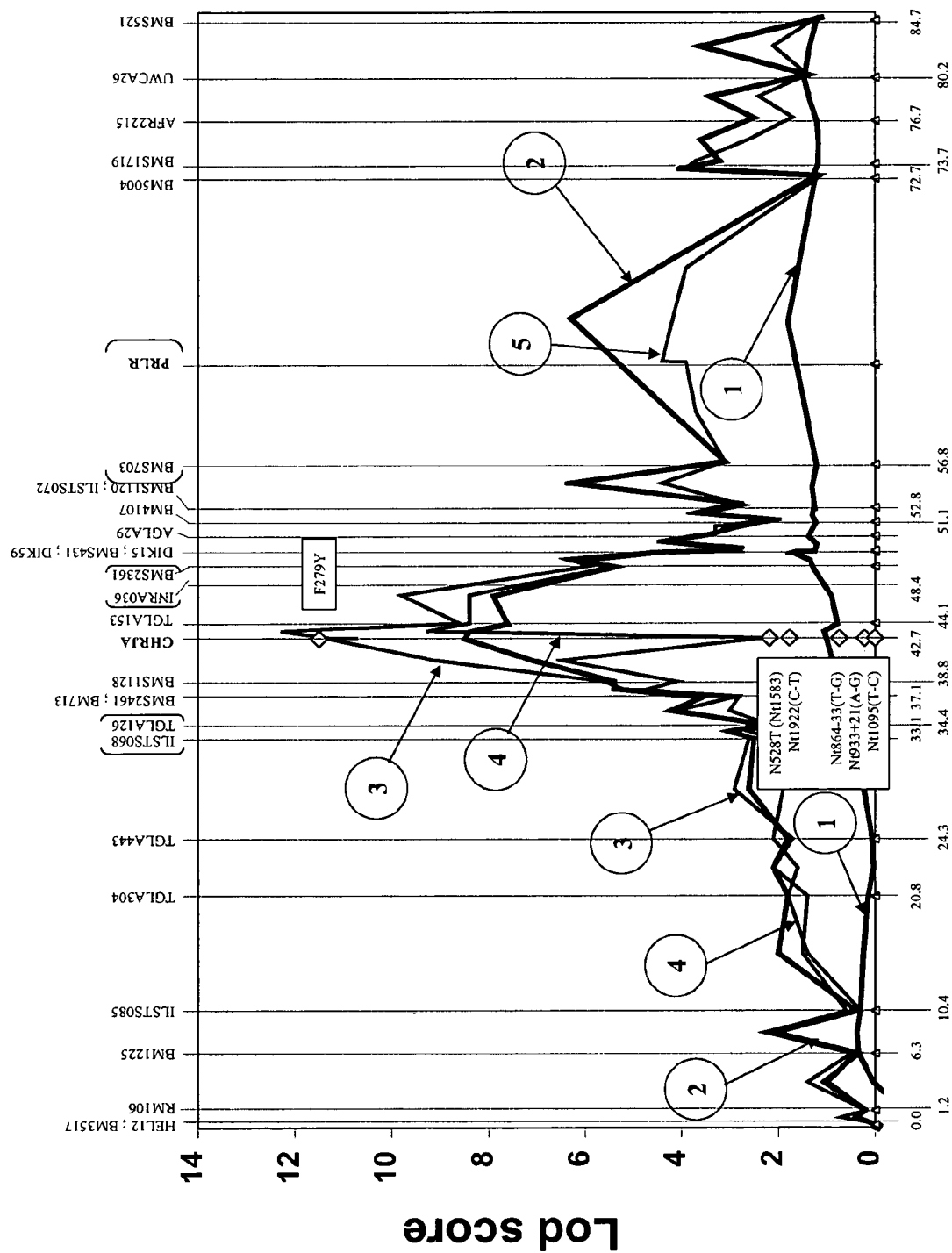
FIG. 2: Shows the lod score profiles obtained for protein percentage along the chromosome 20 map using the LDVCM programs. The name of the markers composing the map is given at the top of the figure and their respective position in centimorgan (Kosambi) at the bottom. The data displayed as curves are delineated by the numbering on the figure. Curve 1 is obtained by considering linkage information only, while all other curves are obtained by considering both linkage and LD. Curve 2: basic chromosome 20 microsatellite marker map. Curve 3: chromosome 20 microsatellite marker map+ six GHR SNPs (F279Y (Nt836), Nt864−33(T-G), Nt933+21 (A-G), Nt1095(T-C), N528T (Nt1583) and Nt1922(C-T)). Curve 4: chromosome 20 microsatellite marker map+five GHR SNPs (Nt836 (F279Y) dropped). Curve 5: chromosome 20 microsatellite marker map+four PRLR SNPs. The diamonds correspond to the lod scores obtained by single-point analysis with the individual GHR SNPs. The names of the corresponding SNPs are given in the adjacent boxes.

To confirm the findings obtained with the haplotype based test for association, we analyzed data set I using the LDVCM program for combined linkage and LD mapping. FIG. 2 shows the locations scores that were obtained with this approach for protein %. The profile obtained when considering linkage information only essentially parallels that obtained by multimarker regression (cfr. FIG. 1), although the lod scores are slightly less significant ($z_{max}$=1.8; chromosome-wide p-value=0.016). When including linkage disequilibrium information, however, a very significant lod score of 8.5 corresponding to a chomosome-wise p-value of 1.5E-8 was obtained at map position 43 cM, i.e. very close to the chromosome region identified by the haplotype-based association test. Using the same approach, highly significant lod score were obtained in the same chromosome region for fat percentage (position: 43 cM; lod score: 5.9; p-value: 7.5E-6), milk yield (position: 43 cM; lod score: 4.5; p-value: 0.00018), fat yield (position: 46 cM; lod score: 3.2; p-value: 0.0047), and protein yield (position: 43 cM; lod score: 5.2; p-value: 3.7E-5)(data not shown). These results therefore supported the existence of a QTL influencing milk yield and composition in the vicinity of the GHR gene.

Scanning the Bovine Growth Hormone Receptor (GHR) Gene for DNA Sequence Polymorphisms.

As it appeared that the GHR gene accounted for at least part of the QTL effect, it was predicted, based on the haplotype-based test for association, that sires 1 and 18 would both be heterozygous for a mutation causing the GHR to be functionally different. It was therefore decided to scan the coding portion of the GHR gene for DNA sequence polymorphisms in these animals. Intronic primers allowing for the convenient amplification and sequencing of exons 3 to 10 of the GHR were developed as described in Materials & Methods. Analysis of the sequence traces obtained from five Holstein-Friesian individuals including sires 1 and 18 revealed ten single nucleotide polymorphisms (SNP) in the GHR gene. FIG. 3 reports the position and nature of the corresponding SNPs.

Four of these are SNPs located in introns (Nt71–85(del1), Nt7–12(T-C), Nt864–33(T-G) and Nt933+21(A-G)), one is an SNP located in the 3'UTR of the GHR gene (Nt1922(C-T)), and three are synonymous mutations in third codon positions (Nt1095(C-T), Nt1635(C-T) and Nt1809(C-T)). None of these are a priori likely to affect the function of the GHR gene. (SEQ ID NO 1 corresponding to part of intron 2 and exon 3, SEQ ID NO 2 corresponding to parts of introns 7 and 8 and exon 8, SEQ ID NO 3 corresponding to parts of introns 8 and 9 and exon 9, SEQ ID NO 4 cDNA.)

The two remaining SNPs, however, modify the amino-acid sequence of the GHR receptor. A T to A substitution in exon VIII results in the non-conservative replacement of a neutral phenylalanine with an uncharged but polar tyrosine residue (F279Y). The corresponding phenylalanine residue is located within the transmembrane domain of the GHR and is conserved amongst all analyzed mammals (human, baboon, rabbit, mouse, rat, dog, pig, sheep, opossum) except guinea-pig where it is nevertheless replaced by a neutral leucine residue. In chicken and pigeon, the corresponding residue is also a neutral isoleucine (For genomic and cDNA sequence see SEQ ID NO 2 and 4 and the amino acid sequence SEQ ID NO 5)

An A to C substitution in exon X results in the replacement of an asparagine with a threonine (N528T), both amino-acids being polar uncharged residues. This residue is less conserved during evolution, being either an asparagine (human, rabbit, pig, chicken) or a serine residue (ovine, mouse, rat). (see SEQ ID NO 4 and 5.)

Sires 1 and 18, which were both heterozygous for the GHR containing marker haplotype associated with a highly significant substitution effect on protein percentage in the association test, were heterozygous for SNPs Nt71–85(dell) (see SEQ ID NO 1), Nt864–33(T-G) (see SEQ ID NO 3), Nt933+21(A-G) (see SEQ ID NO 3) and most importantly Nt836 (F279Y) (see SEQ ID NO 2, 4, and 5). Given the effect of this SNP on the sequence of the GHR gene and therefore possibly on its protein function, F279Y stood out as prime candidate for the mutation causing the observed QTL effect.

Inclusion of SNPs in the Combined Linkage and LD Analysis Dramatically Increases the Lod Score at the GHR Locus.

Figure 4:
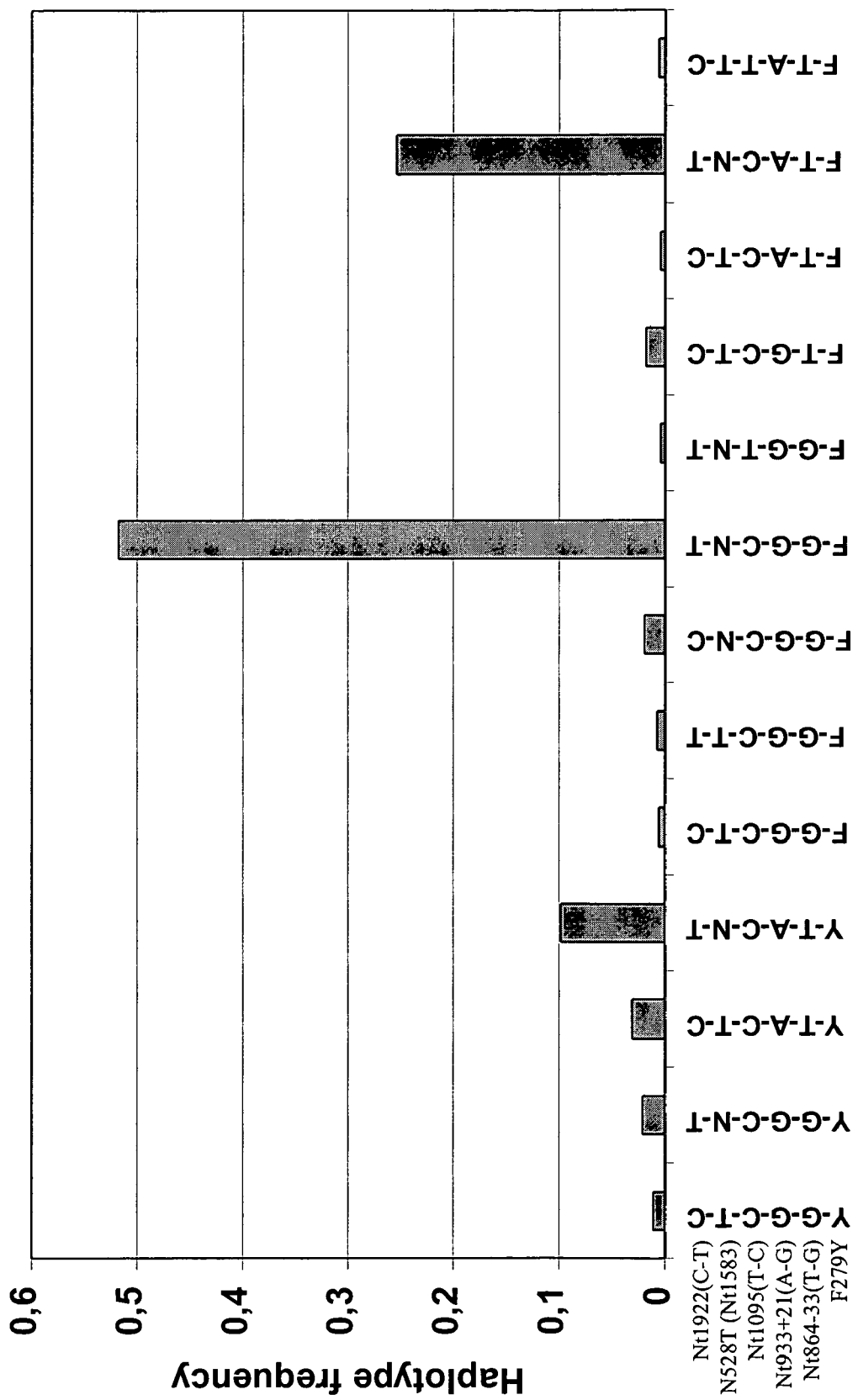
FIG. 4: Shows the frequency distribution of the GHR SNP haplotypes in the Dutch Holstein-Friesian population.

An oligonucleotide ligation assay (OLA) was constructed as described (Karim et al., 2000) for multiplex genotyping of the Nt836 (F279Y), Nt864–33(T-G), Nt933+21(A-G), Nt1095(T-C) (see SEQ ID NO 4), Nt1583 (N528T) (see SEQ ID NO 4) and Nt1922(C-T) (see SEQ ID NO 4) SNPs, and applied it to data set I. The linkage phase was determined as described (Farnir et al., 2002). FIG. 4 shows the frequency distribution of the GHR haplotypes as measured in the maternal chromosomes (MC—see above). It shows that at least 13 distinct haplotypes occur in the Dutch Holstein-Friesian population, however, that three of these account for 85% of the chromosomes in this population.

The GHR SNP haplotype was placed by linkage analysis on the chromosome 20 marker map at position 42.7 cM, coinciding with the GHRJ microsatellite as expected.

A combined linkage and LD analysis was then performed using the LDVCM software, including the new GHR SNP genotypes. As shown in FIG. 2 for protein percentage, inclusion of the GHR SNPs increased the maximum lod score by 3.8 units yielding a maximum lod score of 12.3 at position 43 cM, i.e. just distal of the GHR gene. Table 4 reports the corresponding variance component estimates.

Including the GHR SNPs in the LDVCM analysis had a comparable effect when analyzing fat percentage. The lod score increased from 5.9 to 7.8 maximizing exactly at the GHR gene (as shown in Table 4, below). The effect was more modest for milk yield and fat yield, increasing the lod scores by respectively 0.4 and 0.1 units but maximizing in both instances on the GHR gene (see Table 4 below). Only for protein yield did inclusion of the GHR SNPs resulted in a marked decrease of the lod scores, dropping from 5.2 to 1.7 or less in the region of the GHR gene (see Table 4 below).

For comparison, performing a combined linkage and LD analysis after inclusion of a haplotype composed of four PRLR SNPs resulted in a local decrease in the lod score values for all traits (see FIG. 2 for protein percentage).

33(T-G)), 0.22 (Nt933+21(A-G)), 0 (Nt1095(T-C)), 2.18 (Nt1583 (N528T)) and 1.77 (Nt1922(C-T)) respectively (FIG. 2).

Altogether, these results clearly pointed towards a unique status of the Nt836 (F279Y) polymorphism with regards to the chromosome 20 QTL effect, indicating that this SNP is at least partially responsible for the QTL effect.

Figure 5:
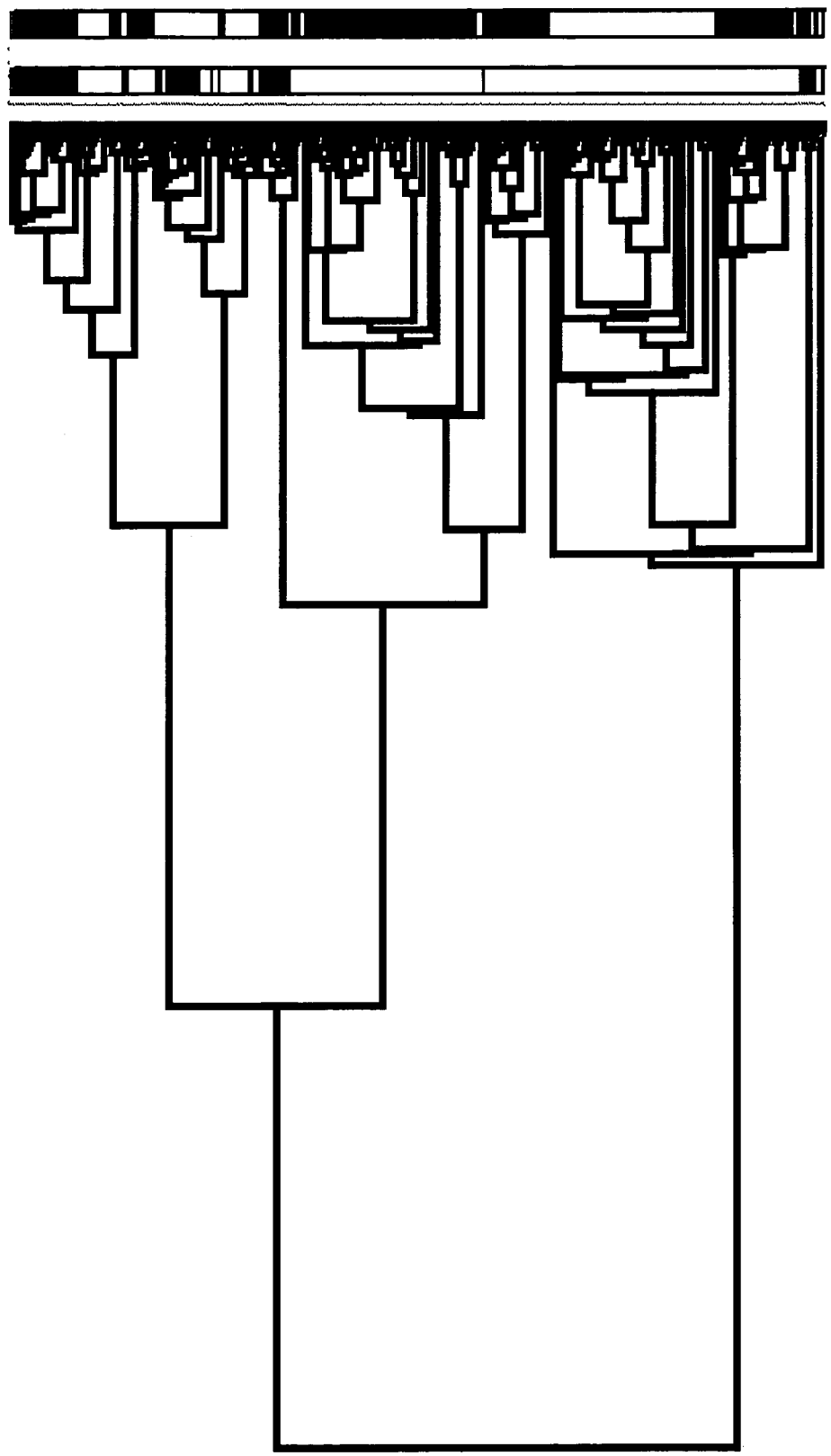
FIG. 5: Shows a UPGMA dendrogram representing the genetic relationship between the SC and MC haplotypes at respective positions 43.4 cM (interval GHR-TGLA53) (dendrogram 5A), and 42.7 cM (dendrogram 5B). The vertical bars correspond to (right) the grouping of the clusters that maximizes the likelihood of the data, and (left) the status of the corresponding haplotype for the nucleotide change resulting in the F279Y mutation (F: white; Y: black).
Figure 5B:
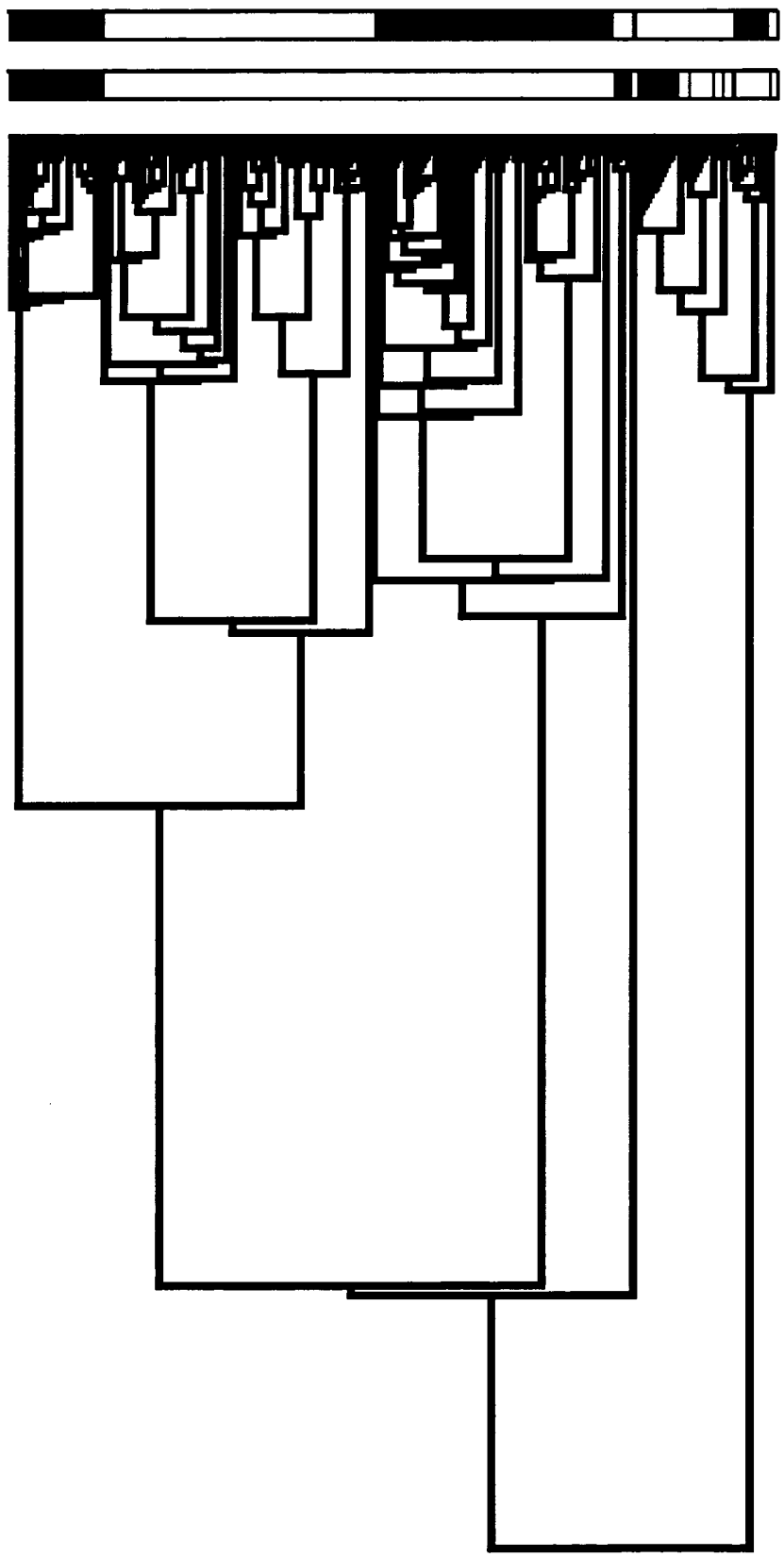

FIG. 5 also shows the segregation of the T (F) and A (Y) alleles within the haplotype clusters maximizing the LDVCM lod scores when analyzing respectively protein and fat percentage including all six GHR SNPs. When analyzing protein percentage, the REML solution is associated with a grouping in 22 haplotype clusters of which 17 are homogeneous with regards to the Nt836 (F279Y) polymorphism. For fat percentage, the corresponding numbers are eight clusters in total of which five are homogeneous for the Nt836 (F279Y) polymorphism.

Effect of the T to A (F279Y) GHR Polymorphism on Milk Yield and Composition in the General Dairy Cattle Population.

To more accurately estimate the effect of the Nt836 (F279Y) GHR polymorphism on milk yield and composition, we genotyped data sets II-VI-corresponding to an additional 2772 bulls and 872 cows—for this SNP. Effects of the Nt836 (F279Y) genotype on DYDs and LVs for milk yield (Kgs),

TABLE 4

Results of the LDVCM analysis after addition of the six GHR SNPs to the BTA20 microsatellite map.

| Trait | Map position | N° of clusters | $r^2$-QTL | Lod score | $r^2$-POLYG | $r^2$-RES |
|---|---|---|---|---|---|---|
| Milk yield (Kgs) | GHR | 21 | 0.06 | 4.9 | 0.72 | 0.22 |
| Fat yield (Kgs) | GHR | 4 | 0.05 | 3.3 | 0.81 | 0.14 |
| Protein yield (Kgs) | GHR | 20 | 0.04 | 1.7 | 0.78 | 0.18 |
| Fat % | GHR | 5 | 0.09 | 7.8 | 0.88 | 0.02 |
| Protein % | GHR-TGLA153 | 22 | 0.10 | 12.3 | 0.87 | 0.03 |

Map position: marker interval alissociated with the highest lod score for the considered trait; N° of clusters: the number of clusters in the haplotype dendrogram that yields the highest lod score; $r^2$-QTL: fraction of the trait variance due to the QTL, computed as $2\sigma_H^2/[2\sigma_H^2+\sigma_A^2+\sigma_E^2]$; $r^2$-POLYG: fraction of the trait variance due to the polygenic background, computed a $\sigma_A^2/[2\sigma_H^2+\sigma_A^2+\sigma_E^2]$; $r^2$-RES: fractiong of the trait unexplained by the model, computed as $\sigma_E^2/[2\sigma_H^2+\sigma_A^2+\sigma_E^2]$.

Unique Status of the Nt836 (F279Y) Polymorphism with Regards to the Chromosome 20 QTL Effect.

Two tests were then performed to determine the relative contribution of the different SNPs to the increase in signal noted for protein percentage. First, the LDVCM analyses were rerun by sequentially dropping one of the six GHR SNPs composing the GHR SNP haplotype. While dropping the Nt864-33(T-G), Nt933+21(A-G), Nt1095(T-C), Nt1583 (N528T) and Nt1922(C-T) SNPs did not significantly alter the lod score profiles (data not shown), dropping the Nt836 (F279Y) SNP virtually annihilated the entire gain obtained by considering the complete GHR SNP haplotype (FIG. 2). Secondly, LDVCM was used to estimate the effects of the different GHR SNPs individually (i.e. without considering flanking marker data): Nt836 (F279Y) yielded a lod score of 11.5 while the other SNPs yielded lod scores of only 0.75 (Nt864- protein yield (Kgs), fat yield (Kgs), protein percentage and fat percentage were estimated using a mixed model including a fixed genotype effect and a random animal model to account for the polygenic background. It can be seen from Table 5, below, that the T to A substitution (F279Y) behaved in a very similar fashion in all analyzed populations, whether Dutch or New Zealander, Holstein-Friesian or Jersey. As expected, the effect of the T to A change (F279Y) was—in all five data sets—most pronounced on protein percentage, accounting for 4% to 8% of the trait variance. The effect of the T to A substitution (F279Y) was also clearly detectable in all these populations on fat percentage and to a lesser extend on milk yield. It accounted for between 1.6% and 6% of the variance in fat percentage and between 0.8% and 4.5% of the variance in milk yield. For milk yield, inheriting one Y allele increased the DYD for milk yield by an estimated 67± Kgs to 112± Kgs and the LV for milk yield by 86± Kgs to 162± Kgs. Effects of the T to A substitution (F279Y) on fat and protein yield were in essence non significant although a tendency towards a decrease in fat yield of 1.5 to 2.5 Kgs for every dose of A (Y) allele was noticeable.

The fact that the T to A substitution (F279Y) showed very comparable effects in all five analyzed populations strongly supports their bona fide nature and the causality of the Nt836 (F279Y) mutation.

TABLE 5

Effect of the GHR Nt836 (F279Y) mutation on milk yield and composition.

| Trait | FY − FF (±SE) | YY − FF (±SE) | $r^2_{QTL}$ | p-value QTL |
|---|---|---|---|---|
| (A) Data sets I + II (Dutch Holstein-Friesian sires - DYDs) | | | | |
| Genotype frequencies: FE: 0.67 – FY: 0.31 —YY: 0.02 – n = 1263 | | | | |
| Milk yield (Kgs) | 67 ± 16 Kgs | 128 ± 49 Kgs | 0.012 | 6.8E−05 |
| Fat yield (Kgs) | −1.4 ± 0.6 Kgs | −4.1 ± 1.8 Kgs | 0.004 | 0.015 |
| Protein yield (Kgs) | −0.1 ± 0.4 Kgs | 0.2 ± 1.3 Kgs | 0.000 | 0.961 |
| Fat % | −0.06 ± 0.01% | −0.14 ± 0.03% | 0.022 | 2.2E−09 |
| Protein % | −0.033 ± 0.01% | −0.06 ± 0.01% | 0.040 | 7.3E−15 |
| (B) Data set III (New Zealand Holstein-Friesian sires - DYDs) | | | | |
| Genotype frequencies: FF: 0.68 – FY: 0.29 – YY: 0.03 – n = 1550 | | | | |
| Milk yield (Kgs) | 89 ± 17 Kgs | 68 ± 45 Kgs | 0.00 1 | 8.4E−06 |
| Fat yield (Kgs) | −1.5 ± 0.7 Kgs | −5.2 ± 1.7 Kgs | 0.009 | 0.01 |
| Protein yield (Kgs) | −1.0 ± 0.5 Kgs | −4.4 ± 1.3 Kgs | 0.009 | 0.007 |
| Fat % | −0.13 ± 0.02% | −0.20 ± 0.02% | 0.016 | 1.2E−12 |
| Protein % | −0.10 ± 0.01% | −0.17 ± 0.04% | 0.081 | 8.0E−32 |
| (C) Data set IV (New Zealand Jersey sires - DYDs) | | | | |
| Genotype frequencies: FF: 0.89 – FY: 0.10 – YY: 0.01 – n = 959 | | | | |
| Milk yield (Kgs) | 112 ± 33 Kgs | 441 ± 102 Kgs | 0.045 | 3.35E−05 |
| Fat yield (Kgs) | 0.1 ± 1.5 Kgs | −2.3 ± 4.7 Kgs | 0.000 | 0.97 |
| Protein yield (Kgs) | 0.3 ± 1.1 Kgs | 6.3 ± 3.3 Kgs | 0.005 | 0.31 |
| Fat % | −0.19 ± 0.05% | −0.68 ± 0.02% | 0.058 | 5.62E−05 |
| Protein % | −0.13 ± 0.02% | −0.30 ± 0.08% | 0.084 | 1.1E−07 |
| (D) Data set V (New Zealand Holstein-Friesian cows - LVs) | | | | |
| Genotype frequencies: FF: 0.73 – FY: 0.24 – YY: 0.03 – n = 485 | | | | |
| Milk yield (Kgs) | 87 ± 48 Kgs | 99 ± 129 Kgs | 0.008 | 0.17 |
| Fat yield (Kgs) | −1.3 ± 2.2 Kgs | −8.3 ± 5.9 Kgs | 0.003 | 0.34 |
| Protein yield (Kgs) | −0.6 ± 1.5 Kgs | −3.1 ± 4.1 Kgs | 0.001 | 0.73 |
| Fat % | −0.14 ± 0.05% | −0.31 ± 0.13% | 0.023 | 0.004 |
| Protein % | −0.10 ± 0.02% | −0.19 ± 0.06% | 0.055 | 2.3E−06 |
| (E) Data set VI (New Zealand Jersey cows - LVs) | | | | |
| Genotype frequencies: FF: 0.81 – FY: 0.17 – YY: 0.02 – n = 387 | | | | |
| Milk yield (Kgs) | 162 ± 52 Kgs | 59 ± 135 Kgs | 0.022 | 0.009 |
| Fat yield (Kgs) | −2.1 ± 2.7 Kgs | −8.3 ± 6.9 Kgs | 0.007 | 0.40 |
| Protein yield (Kgs) | 1.2 ± 1.7 Kgs | −1.4 ± 4.5 Kgs | 0.001 | 0.73 |
| Fat % | −0.28 ± 0.06% | −0.33 ± 0.17% | 0.058 | 6.7E−05 |
| Protein % | −0.13 ± 0.03% | −0.10 ± 0.07% | 0.068 | 1.6E−05 |

(i) FY-FF: difference between the mean trait values of the FY and FF genotypes=effect of one Y dose; (ii) YY-FF: difference between the mean trait values of the YY and FF variants=effect of two Y doses; (iii) $r^2_{QTL}$: proportion of the trait variance explained by the GHR F279Y variation; (iv) p-value QTL: statistical significance of the GHR F279Y variant effect. Note that the absolute values of the effects on the percentage traits cannot be directly compared between data sets I+II (Netherlands) versus data sets III-VI (New Zealand) as the percentage traits are computed from the yield traits using different formulas in both countries.

CONCLUSIONS

Strong evidence is provided that the GHR gene accounts at least in part for the QTL effect that was previously reported on bovine chromosome 20 (Georges et al., 1995; Arranz et al., 1998). The non-conservative substitution of a highly conserved F residue in the transmembrane domain suggests that the F279Y polymorphism may be the direct cause of the consistently sociated effects on milk yield and composition. The F279Y polymorphism also effect live weight. In an across breed analysis (Holstein-Friesian, Jersey and Ayrshire) the T allele (F amino acid) increased the live weight by 1.9 kg, which is significant at the 5% level. This is compatible with a direct effect of the GHR.

The effects of the F279Y amino acid allelic state on the indices that are used as the basis for selection in the Netherlands and New Zealand (INET and breeding worth (BW) respectively) are highly significant. As a matter of fact, a retrospective survey of the genotype of the New Zealand sires clearly indicates that the frequency of the T allele has increase in recent years and that the TT genotype increases the likelihood for a sire to be selected for breeding (Table 6). As a consequence, we anticipate that this marker has the potential to be very useful for marker assisted selection and to more effectively increase the frequency of the favourable T allele.

TABLE 6

Genotype frequencies of bulls that are progeny tested selected for commercial use based on breeding worth.

| | Progeny tested bulls | | | Selected bulls | | |
|---|---|---|---|---|---|---|
| Breed/SPS year | AA | AT | TT | AA | AT | TT |
| Holstein-Friesian | | | | | | |
| 1994 | 3 | 19 | 62 | 0 | 1 | 9 |
| 1995 | 1 | 24 | 87 | 0 | 1 | 5 |
| 1996 | 1 | 36 | 100 | 0 | 2 | 13 |

TABLE 6-continued

Genotype frequencies of bulls that are progeny tested selected for commercial use based on breeding worth.

| Breed/SPS year | Progeny tested bulls | | | Selected bulls | | |
| --- | --- | --- | --- | --- | --- | --- |
| | AA | AT | TT | AA | AT | TT |
| Jersey | | | | | | |
| 1994 | 2 | 5 | 46 | 0 | 0 | 9 |
| 1995 | 0 | 7 | 55 | 0 | 0 | 7 |
| 1996 | 1 | 18 | 36 | 0 | 1 | 5 |
| 1997 | 1 | 10 | 89 | 0 | 0 | 6 |

Data sets V and VI (composed of cows) allowed for the analysis of potential dominance effects between the F and Y allele. Modest evidence in favor of dominance of the Y over the F allele was found for protein percentage (p<0.05; data not shown). However, as the number of YY individuals were small, the power to detect significant dominance interactions was very limited. Preliminary analyses in these data sets also suggest that the Nt836 (F279Y) mutation and the previously described K232A mutation in the bovine DGAT gene (Grisart et al., 2002), act in an additive manner.

We believe it unlikely that the F279Y variation accounts for the entire chromosome 20 QTL effect. Indeed, examination of the location scores (e.g. FIG. 1), suggests that additional more distally located genes might contribute to the QTL effect on BTA20 as well. We have also identified two sires that would clearly be heterozygous for a QTL on BTA20 despite being homozygous for the Nt836 (F279Y) polymorphism (data not shown).

It will be appreciated that it is not intended to limit the invention to the above examples only, many variations, which may readily occur to a person skilled in the art, being possible without departing from the scope thereof as defined in the accompanying claims.

INDUSTRIAL APPLICABILITY

The present invention is directed to methods of genotyping bovine to facilitate the selection of animals with altered milk production and carcass traits. In particular, such traits include altered milk volume, milk protein content and milkfat content and increased or decreased live weight. It is anticipated that herds of bovine selected for such traits will produce an increased milk and live weight, or altered characteristics for particular applications, and therefore be of significant economical benefit to farmers. Semen and embryos of such selected animals will also be useful for selective breeding purposes.

REFERENCES

Andersson, L. 2001. Genetic dissection of phenotypic diversity in farm animals. *Nature Reviews Genetics* 2: 130-138.

Arranz, J.-J.; Coppieters, W.; Berzi, P.; Cambisano, N.; Grisart B.; Karim, L.; Marcq, F.; Riquet, J.; Simon, P.; Vanmnashoven, P.; Wagenaar, D.; Georges, M. (1998) A QTL affecting milk yield and composition maps to bovine chromosome 20: a confirmation. *Animal Genetics* 29: 107-115.

Barendse, W.; Armitage, S. M.; Kossarek, L. M.; Shalom, A.; Kirkpatrick, B. W.; Ryan, A. M.; Clayton, D.; Li, L.; Neibergs, H. L.; Zhang, N.; Grosse, W. M.; Weiss, J.; Creighton, P.; Mccarthy, F.; Ron, M.; Teale, A. J.; Fries, R.; Mcgraw, R. A.; Moore, S. S.; Georges, M,; Soller, M.; Womack, J. E.; Hetzel, D. J. S. (1994). A genetic linkage map of the bovine genome. *Nature Genet.* 6: 227-235.

Bauman, D. E.; Everett, R. W.; Weiland, W. H.; Collier, R. J. (1999). Production responses to bovine somatotropin in Northeast dairy herds. *J Dairy Sci* 82: 2564-2573.

Bishop, M. D.; Kappes, S. M.; Keele, J. W.; Stone, R. T.; Sunden, S. L. F.; Hawkins, G. A.; Solinas Toldo, S.; Fries, R.; Grosz, M. D.; Yoo, J.; Beattie, C. W. (1994). A genetic linkage map for cattle. *Genetics* 136: 619-639.

Churchill, G. A. & Doerge, R. W. (1995). Empirical threshold values for quantitative trait mapping. *Genetics* 138: 963-971.

Collins, F. S. (1995). Positional cloning moves from perditional to traditional. *Nature Genet.* 9: 347-350.

Coppieters, W.; Riquet, J.; Arranz, J.-J.; Berzi, P.; Cambisano, N.; Grisart, B.; Karim, L.; Marcq, F.; Simon, P.; Vanmanshoven, P.; Wagenaar, D.; Georges, M. (1998a) A QTL with major effect on milk yield and composition maps to bovine chromosome 14. *Mammalian Genome* 9: 540-544.

Coppieters, W.; Riquet, J.; Arranz, J.-J.; Berzi, P.; Cambisano, N.; Grisart, B.; Karim, L.; Marcq, F.; Simon, P.; Vanmanshoven, P.; Wagenaar, D.;Georges, M. (1998) A QTL with major effect on milk yield and composition maps to bovine chromosome 14. *Mammalian Genome* 9: 540-544.

Darvasi, A. (1998). Experimental strategies for the genetic dissection of complex traits in animal models. *Nat Genet.* 18(1):19-24.

Falconer D. S. and Mackay T. F. C. Introduction to Quantitative Genetics, 4$^{th}$ Edition. Longman Scientific and Technical, New York, 1996.

Farnir, F.; Grisart, B.; Coppieters, W.; Riquet, J.; Berzi, P.; Cambisano, N.; Karim, L.; Mni, M.; Simon, P.; Wagenaar, D.; Georges, M. (2000). Simultaneous mining of linkage and linkage disequilibrium to fine-map QTL in outbred half-sib pedigrees: revisiting the location of a QTL with major effect on milk production on bovine chromosome 14. Ph.D *Thesis, University of Liege* 2000.

Farnir, F., B. Grisart, W. Coppieters, J. Riquet, P. Berzi, N. Cambisano, L. Karim, M. Mni, S. Moisio, P. Simon, D. Wagenaar, J. Vilkki and M. Georges. 2002. Simultaneous mining of linkage and linkage disequilibrium to fine-map QTL in outbred half-sib pedigrees: revisiting the location of a QTL with major effect on milk production on bovine chromosome 14. Genetics (In press).

Flint, J. and Mott, R. 2001. Finding the molecular basis of quantitative traits: successes and pitfalls. *Nature Reviews Genetics* 2: 437-445.

Georges, M.; Nielsen, D.; Mackinnon, M.; Mishra, A.; Okimoto, R.; Pasquino, A. T.; Sargeant, L. S.; Sorensen, A.; Steele, M. R.; Zhao, X.; Womack, J. E.; Hoeschele, I. (1995) Mapping quantitative trait loci controlling milk production by exploiting progeny testing. *Genetics* 139: 907-920.

Georges, M.; Andersson, L. (1996). Livestock genomics comes of age. *Genome Research.* 6: 907-921.

Godowski, P. J.; Leung, D. W.; Meacham, L. R.; Galgani, J. P.; Hellmiss, R.; Keret, R.; Rotwein, P. S.; Parks, J. S.; Laron, Z. and Wood, W. I. (1989) Characterization of the human growth hormone receptor gene and demonstration of a partial gene deletion in two patients with Laron-type dwarfism. *Proc. Natl. Acad. Sci. U.S.A.* 86 (20), 8083-8087.

Grisart, B.; Coppieters, W.; Farnir, F.; Karim, L.; Ford, C.; Cambisano, N.; Mni, M.; Reid, S.; Spelman, R.; Georges, M. & Snell, R. (2002). Positional candidate cloning of a QTL in dairy cattle: Identification of a missense mutation in the bovine DGAT gene with major effect on milk yield and composition. *Genome Research* 12: 222-231.

Hauser, S. D.; McGrath, M. F.; Collier, R. J. and Krivi, G. G. (1990) Cloning and in vivo expression of bovine growth hormone receptor MRNA. *Molecular and Cellular Endocrinology* 72, 187-200.

Heap, D.; Lucy, M. C.; Collier, R. J.; Boyd, C. K. & Warren, W. C. (1995) Nucleotide sequence of the promoter and first exon of the somatotropin receptor gene in cattle. *Journal of Animal Science* 73: 1529.

Hudson, R. R. 1985. The sampling distribution of linkage disequilibrium under an infinite alleles model without selection. *Genetics* 109:611-631.

Johnson, D. L.; Thompson, R. 1995. Restricted maximum likelihood estimation of variance components for univariate animal models using sparse matrix techniques and average information. *J Dairy Sci*. 78: 449-456.

Kappes, S. M.; Keele, J. W.; Stone, R. T.; Mcgraw, R. A.; Sonstegard, T. S.; Smith, T. P. L.; Lopez-Corrales, N. L.; Beattie, C. W. (1997) A Second-Generation Linkage Map of the Bovine Genome. *Genome Research* 7: 235-249.

Karim, L.; Coppieters, W.; Grobet, L.; Valentini, A.; Georges, M. (2000). Convenient genotyping of six myostatin mutations causing double-muscling in cattle using a multiplex oligonucleotide ligation assay. *Animal Genetics* 31: 396-399.

Kim, J. J.; Georges, M. (2002). Evaluation of a new fine-mapping method exploiting linkage disequilibrium: a case study analysing a QTL with major effect on milk composition on bovine chromosome 14. Submitted for publication Knott, S.; J. M. Elsen and Haley, C. (1996) Methods for multiple marker mapping of quantitative trait loci in half-sib populations. *Theoretical and Applied Genetics* 93, 71-80.

Lynch M and Walsh B (1997). Genetics and analysis of quantitative traits. Sinuaer Associates, Inc. Sunderland, Massachusetts.

Mackay, T. F. C. 2001. Quantitative Trait Loci in Drosophila. *Nature Reviews. Genetics* 2: 11-20.

Mauricio, R. 2001. Mapping quantitative trait loci in plants: uses and caveats for evolutionary biology. *Nature Reviews. Genetics* 2: 370-381.

Meuwissen T H, Goddard M E. (2000). Fine mapping of quantitative trait loci using linkage disequilibria with closely linked marker loci. *Genetics* 155:421-430.

Meuwissen T H, Goddard M E. (2001). Prediction of identity by descent probabilities from marker-haplotypes. *Genet Sel Evol* 33:605-634.

Mount, D. W. 2001. Bioinformatics: Sequence and Genome analysis. Cold Spring Harbor Laboratory Press, New York, N.Y.

Sambrook, J.; Fritsch, E. F.; Maniatis, T. (1989). *Molecular Cloning: A Laboratory Manual*. Cold Spring Harbour Lab Press, Cold Spring Harbour, N.Y.

Spelman, R. J., W. Coppieters, L. Karim, J. A. M. van Arendonk, and H. Bovenhuis, (1996). Quantitative trait loci analysis for five milk production traits on chromosome six in the Dutch Holstein-Friesian population. *Genetics* 144: 1799-1808.

Spielman, R. S.; McGinnis, R. E.; Ewens, W. J. (1993). Transmission test for linkage disequilibrium: the insulin gene region and insulin-dependent diabetes mellitus (IDDM). *Am J Hum Genet* 52:506-516.

Stewart, A. J.; Canitrot, Y.; Baracchini, E.; Dean, N. M.; Deeley, R. G. and Cole, S. P. C. (1996). Reduction of expression of the multidrug resistance protein (MRP) in human tumour cells by antisense phophorothioate oligonucleotudes. Biochem. *Pharmacol*. 51: 461-469.

Van Raden, P. M. & Wiggans, G. R. (1991) Derivation calculation and use of National Animal Model Information. *J. Dairy Sci*. 74:2737-2746.

Visscher, P. M.; Thompson, R.; Haley, C. S. (1996) Confidence intervals in QTL mapping by bootstrapping. *Genetics* 143: 1013-1020.

Warren, W.; Smith, T. P.; Rexroad, C. E. $3^{rd}$; Fahrenkrug, S. C.; Allison, T.; Shu, C. L.; Catanese, J.; de Jong, P. J. (2000) Construction and characterization of a new bovine bacterial artificial chromosome library with 10 genome-equivalent coverage. *Mammalian Genome* 11: 662-663.

---

We claim:

1. A method of selecting a bovine, with a genotype indicative of at least one altered milk production trait, the method comprising the steps:
   a) identifying a bovine with thymidine at polymorphic nucleotide position 658 in the growth hormone receptor (GHR) gene of SEQ ID NO: 2, wherein the codon including the thymidine at nucleotide position 658 of SEQ ID NO: 2 encodes phenylalanine at amino acid position 279 in SEQ ID NO: 5; and correlating the presence of the thymidine at position 658 of SEQ ID NO: 2 with at least one altered milk production trait selected from: i) increased milk volume; ii) decreased percentage of milk protein; and iii) decreased percentage of milk fat; and
   b) selecting the bovine on the basis of the identification and correlation in a).

2. A method of selecting a bovine, with a genotype indicative of at least one altered milk production trait, the method comprising the steps:
   a) identifying a bovine with adenosine at polymorphic nucleotide position 658 in the growth hormone receptor (GHR) gene of SEQ ID NO: 2, wherein the codon including the adenosine at nucleotide position 658 of SEQ ID NO: 2 encodes tyrosine at amino acid position 279 in SEQ ID NO: 5; and correlating the presence of the adenosine at position 658 of SEQ ID NO: 2 with at least one altered milk production trait selected from: i) decreased milk volume; ii) increased percentage of milk protein; and iii) increased percentage of milk fat; and
   b) selecting the bovine on the basis of the identification and correlation in a).

3. The method of claim 1, wherein the identification is made by detecting, in a nucleic acid derived from the bovine the presence of thymidine at polymorphic nucleotide position 658 in the GHR gene of SEQ ID NO: 2.

4. The method of claim 2, wherein the identification is made by detecting, in a nucleic acid derived from the bovine the presence of adenosine at polymorphic nucleotide position 658 in the GHR gene of SEQ ID NO: 2.

5. The method of claim 3 or 4, wherein detection is made via amplification of a nucleic acid sequence comprising the polymorphic nucleotide position 658 in the growth hormone receptor (GHR) gene of SEQ ID NO: 2.

6. The method of claim 5, wherein primers consisting of SEQ ID NOs: 6 and 7 are used in the amplification.

7. The method of claim 3, wherein detection is made using an oligonucleotide ligation assay (OLA).

8. The method of claim 7, wherein the OLA is performed using a primer comprising the sequence of any one of SEQ ID NOs: 13 or 14.

9. The method of claim 4, wherein detection is made using an oligonucleotide ligation assay (OLA).

10. The method of claim 9, wherein the OLA is performed using a primer comprising the sequence of anyone of SEQ ID NOs: 12 or 14.

11. The method of claim 3 or 4, further comprising the step of hybridizing a probe to the nucleic acid derived from the bovine, wherein the probe:
   a) comprises at least 5 contiguous nucleotides of positions 599-702 of SEQ ID NO: 2, wherein said 5 contiguous nucleotides comprises either thymidine or adenosine at the position corresponding to the polymorphic nucleotide position 658 in the GHR gene of SEQ ID NO: 2, and
   b) is sufficiently complementary with said nucleic acid so as to bind thereto in 6x sodium citrate/sodium chloride (SSC) at 45° C.;
wherein binding of the probe to the nucleic acid derived from the bovine indicates the presence of specific nucleotide content at the polymorphic nucleotide position 658 of SEQ ID NO: 2.

* * * * *

SEQUENCE LISTING

```
<160> NUMBER OF SEQ ID NOS: 62

<210> SEQ ID NO 1
<211> LENGTH: 762
<212> TYPE: DNA
<213> ORGANISM: bovine
<220> FEATURE:
<221> NAME/KEY: misc_feature
<222> LOCATION: (6)..(6)
<223> OTHER INFORMATION: A, T, C or G
<220> FEATURE:
<221> NAME/KEY: variation
<222> LOCATION: (728)..(728)
<223> OTHER INFORMATION: T->C variation in intron 2, 12 base pairs
      upstream (5') of cDNA base 71.
<220> FEATURE:
<221> NAME/KEY: variation
<222> LOCATION: (655)..(655)
<223> OTHER INFORMATION: deletion of nucleotide thymine in intron 2, 85
      base pairs upstream (5') of cDNA base 71.
<220> FEATURE:
<221> NAME/KEY: misc_feature
<222> LOCATION: (21)..(21)
<223> OTHER INFORMATION: A, T, C or G
<220> FEATURE:
```

```
<221> NAME/KEY: misc_feature
<222> LOCATION: (25)..(25)
<223> OTHER INFORMATION: A, T, C or G
<220> FEATURE:
<221> NAME/KEY: misc_feature
<222> LOCATION: (33)..(33)
<223> OTHER INFORMATION: A, T, C or G
<220> FEATURE:
<221> NAME/KEY: misc_feature
<222> LOCATION: (72)..(72)
<223> OTHER INFORMATION: A, T, C or G
<220> FEATURE:
<221> NAME/KEY: misc_feature
<222> LOCATION: (76)..(76)
<223> OTHER INFORMATION: A, T, C or G
<220> FEATURE:
<221> NAME/KEY: misc_feature
<222> LOCATION: (121)..(121)
<223> OTHER INFORMATION: A, T, C or G
<220> FEATURE:
<221> NAME/KEY: misc_feature
<222> LOCATION: (159)..(159)
<223> OTHER INFORMATION: A, T, C or G
<220> FEATURE:
<221> NAME/KEY: misc_feature
<222> LOCATION: (756)..(756)
<223> OTHER INFORMATION: A, T, C or G
<220> FEATURE:
<221> NAME/KEY: misc_feature
<222> LOCATION: (758)..(758)
<223> OTHER INFORMATION: A, T, C or G

<400> SEQUENCE: 1 ggggganttcc catggtggtc nagcngttaa agngtctgta tagaatgcaa gaagacccag      60
gtttgatccc tngggnaaga aagatcccTT gggagaagga aaatggcaat ccactcccag     120
nactattggc tggaaatgcc atggacaaag gagcctggna ggttacagtc catggggtcg     180
caaagagttg acacgactga gcgacttcac tttgaatact agtatcagta ccattagaac     240
tcctttataa tagatgactc attgcccatc tcatgtccta aagttctgtc tctccctctt     300
gtccagtttt tcacttcccc tcattccttc cctactccca gggttgctca catgtttgtt     360
tctaagaata aacgtgtttg actgaactgt ttttaatact gcttttaaaa agaatttatg     420
ttccttcttg ttttcacaag caagacttaa gtttggaccc aaatgatgta ggaaggcaat     480
ttttcatcct tcctaactgt gtccaggcat gagaccagag gcaactaaac aaaaggtttc     540
catttgctct gaatatttag gagttccttt tagaggatag gtgcaatttt agttttgaaa     600
agaaagaaaa aagaagagaa ttttgtgag gttgggccag gtcacatgtt gacattttga     660
aaatgagaat gtaacaaggt cacatcagac cattttcac agggggtgact aagggttttt     720 tccctctttt gtctttcagc cacaccagct ttcctncnaa at                         762

<210> SEQ ID NO 2
<211> LENGTH: 1437
<212> TYPE: DNA
<213> ORGANISM: Bos taurus
<220> FEATURE:
<221> NAME/KEY: primer_bind
<222> LOCATION: (466)..(490)
<223> OTHER INFORMATION: 1UP primer bind site
<220> FEATURE:
<221> NAME/KEY: primer_bind
<222> LOCATION: (782)..(806)
<223> OTHER INFORMATION: 1DN primer bind site
<220> FEATURE:
<221> NAME/KEY: primer_bind
<222> LOCATION: (599)..(628)
<223> OTHER INFORMATION: AdaraforAD primer bind site
<220> FEATURE:
<221> NAME/KEY: primer_bind
```

```
<222> LOCATION: (673)..(702)
<223> OTHER INFORMATION: AdararevAD primer bind site
<220> FEATURE:
<221> NAME/KEY: primer_bind
<222> LOCATION: (646)..(665)
<223> OTHER INFORMATION: Probe1 Adara1 bind site
<220> FEATURE:
<221> NAME/KEY: primer_bind
<222> LOCATION: (646)..(665)
<223> OTHER INFORMATION: Probe2 Adara2 bind site
<220> FEATURE:
<221> NAME/KEY: primer_bind
<222> LOCATION: (659)..(681)
<223> OTHER INFORMATION: Oligo ligation assay common probe C (-P) bind
      site
<220> FEATURE:
<221> NAME/KEY: primer_bind
<222> LOCATION: (659)..(681)
<223> OTHER INFORMATION: 1C bind site
<220> FEATURE:
<221> NAME/KEY: primer_bind
<222> LOCATION: (639)..(658)
<223> OTHER INFORMATION: 1AS1 (-Fam) bind site
<220> FEATURE:
<221> NAME/KEY: primer_bind
<222> LOCATION: (639)..(658)
<223> OTHER INFORMATION: 1AS2 (-Hex) bind site
<220> FEATURE:
<221> NAME/KEY: misc_feature
<222> LOCATION: (1190)..(1190)
<223> OTHER INFORMATION: n (a, t, c or g)
<220> FEATURE:
<221> NAME/KEY: misc_feature
<222> LOCATION: (1293)..(1293)
<223> OTHER INFORMATION: n (a, t, c or g)
<220> FEATURE:
<221> NAME/KEY: misc_feature
<222> LOCATION: (1321)..(1321)
<223> OTHER INFORMATION: n (a, t, c or g)
<220> FEATURE:
<221> NAME/KEY: variation
<222> LOCATION: (658)..(658)
<223> OTHER INFORMATION: Base "T" at position 658 is changed to "A". The
      encoded amino acid is therefore changed from F (TTT,
      Phenylalanine) to Y (TAT, Tyrosine).

<400> SEQUENCE: 2
ggatccaaat atggggacaa gggaaagtgt aggaagattg aggaaaagaa aggatgaaga      60
ccgagggtaa gcgcgttccc agaaagctaa ggtagactta aggattggac ccctcgaaac    120
gagggagttt tattaataaa ccccccaaat caggctggcc cccaacgttg tggggggccc    180
caaaccagaa gaagactaag gccgaaggac cccggggagg aggggaggag ttggcagaat    240
ttaggggaag taagaggatg cccagcaacg cttttccctc cagctagagc ctttgatggc    300
acgccctggg cacataagat ggtagaggac ggggtttgta aataatagac atggaatgtt    360
cctagaatgg attctgagac ccctgattag gtggtatgct aagggatctg aagaagtggg    420
atagagatgt tcttagaaaa tgcttagtaa ttgcattcta tttcagtggc tatcaagtga    480
aatcattgac tttactagat gaagacaaat tagggagttt tatgtgggac aggaggatga    540
gatataaact tcaactgttc atagttctgt gagatattat ttttgtgttt tcagatttcc    600
agtttccatg gttcttaatt attatctttg gaatacttgg gctagcagtg acattatatt    660
tactcatatt ttctaaacag caaaggtaag tgtgatataa cctactctga tatgttttgc    720
cagttattta gcaaatgtcc atgtttccat tttttgtttg atgttttctt ttgtgaatcc    780
tgagtgaagt gtttcatcaa cccagtgaaa cgttatcgct ctacatttac atctttgttg    840
tgtccacaga gagacaacac aggtctcagt tttatctgga aagttgcata ggatgttaag    900
agggtgaggc tagtgactac ataccatgtg acatgcacct taaagttccg cactgatatt    960
```

-continued

```
tattccagga cccagaggta gctttgagca aaaatttaag tggtgaacta aagctactag    1020
ataattcagt ctaataaaac cttctttag acttcatatg ataccaatct taagtaaatt    1080
tgggtttatt taaattggtt ggctacttac agtttggtat tttaccttct tttgcagaga    1140
taaaattcta agtttgagga caccatcctg catcctcttg cagccagaan gcaggtttca    1200
gttattattc tgccactgtt ggttgagttc atttgagtcc ctttatctct aggactccac    1260
gttctcatgg gtaatttgag ggtggtggat tgnatgatgt ttaagtttcc cttaactgta    1320
ngaccattat tctattttca ttcttgaaag aaactcagta tagactacag aaacttttaa    1380
tccaaaatac tggaaaaagt acctggtgtg ggtggcaggt tttttacatt aaaaaat      1437
```

<210> SEQ ID NO 3
<211> LENGTH: 444
<212> TYPE: DNA
<213> ORGANISM: Bos taurus
<220> FEATURE:
<221> NAME/KEY: variation
<222> LOCATION: (179)..(179)
<223> OTHER INFORMATION: T->G variation in intron 8, 33 base pairs
      upstream (5') of cDNA base 864.
<220> FEATURE:
<221> NAME/KEY: primer_bind
<222> LOCATION: (51)..(70)
<223> OTHER INFORMATION: 2UP primer bind site
<220> FEATURE:
<221> NAME/KEY: primer_bind
<222> LOCATION: (338)..(357)
<223> OTHER INFORMATION: 2DN primer bind site
<220> FEATURE:
<221> NAME/KEY: primer_bind
<222> LOCATION: (158)..(179)
<223> OTHER INFORMATION: 2AS1 primer bind site
<220> FEATURE:
<221> NAME/KEY: primer_bind
<222> LOCATION: (158)..(179)
<223> OTHER INFORMATION: 2AS2 primer bind site
<220> FEATURE:
<221> NAME/KEY: primer_bind
<222> LOCATION: (180)..(203)
<223> OTHER INFORMATION: 2C primer bind site
<220> FEATURE:
<221> NAME/KEY: primer_bind
<222> LOCATION: (51)..(70)
<223> OTHER INFORMATION: 3UP primer bind site
<220> FEATURE:
<221> NAME/KEY: primer_bind
<222> LOCATION: (338)..(357)
<223> OTHER INFORMATION: 3DN primer bind site
<220> FEATURE:
<221> NAME/KEY: primer_bind
<222> LOCATION: (278)..(302)
<223> OTHER INFORMATION: 3AS1 primer bind site
<220> FEATURE:
<221> NAME/KEY: primer_bind
<222> LOCATION: (278)..(302)
<223> OTHER INFORMATION: 3AS2 primer bind site
<220> FEATURE:
<221> NAME/KEY: primer_bind
<222> LOCATION: (303)..(326)
<223> OTHER INFORMATION: 3C primer bind site
<220> FEATURE:
<221> NAME/KEY: variation
<222> LOCATION: (302)..(302)
<223> OTHER INFORMATION: A->G variation in intron 9, 21 base pairs
      downstream (3') of cDNA base 933

<400> SEQUENCE: 3

```
ttttatttaa attcacttca gatgagggtt ttttccatt ctttagtttt gcctcatcat    60
tcactgctta atgcttttcc ttctctttct cagattcact tattccaaat attctgttac   120
```

```
tttatattag taataatatt gtcaatattt tatttctgtc ttttgaaatg agaatgagta    180
acttacatca aaacaaaatt ttgttttcaa ggattaagat gctgattcta cccccagttc    240
cagttccaaa gattaaagga attgatccag atctcctcaa ggtaattaat aaaatatcta    300
aattgtacat gacactaatt aaatgttacc ttaagaacag agccttatgt tgaaaccttt    360
tgcaagctat atgtatcaca ttaaatttt tgtattcctt ctgggaaaag ttttaaata    420 atacatccct taaaattatg agga                                          444
```

```
<210> SEQ ID NO 4
<211> LENGTH: 2201
<212> TYPE: DNA
<213> ORGANISM: Bos taurus
<220> FEATURE:
<221> NAME/KEY: variation
<222> LOCATION: (836)..(836)
<223> OTHER INFORMATION: T->A variation results in a phenylalanine to
      tyrosine substitution in the amino acid sequence
<220> FEATURE:
<221> NAME/KEY: primer_bind
<222> LOCATION: (1009)..(1033)
<223> OTHER INFORMATION: 4UP primer bind site
<220> FEATURE:
<221> NAME/KEY: primer_bind
<222> LOCATION: (1183)..(1206)
<223> OTHER INFORMATION: 4DN primer bind site
<220> FEATURE:
<221> NAME/KEY: primer_bind
<222> LOCATION: (1077)..(1095)
<223> OTHER INFORMATION: 4AS1 primer  bind site
<220> FEATURE:
<221> NAME/KEY: primer_bind
<222> LOCATION: (1077)..(1095)
<223> OTHER INFORMATION: 4AS2 primer bind site
<220> FEATURE:
<221> NAME/KEY: primer_bind
<222> LOCATION: (1096)..(1116)
<223> OTHER INFORMATION: 4C primer bind site
<220> FEATURE:
<221> NAME/KEY: primer_bind
<222> LOCATION: (1463)..(1487)
<223> OTHER INFORMATION: 5UP primer bind site
<220> FEATURE:
<221> NAME/KEY: primer_bind
<222> LOCATION: (1685)..(1708)
<223> OTHER INFORMATION: 5DN primer bind site
<220> FEATURE:
<221> NAME/KEY: primer_bind
<222> LOCATION: (1566)..(1583)
<223> OTHER INFORMATION: 5AS1 primer bind site
<220> FEATURE:
<221> NAME/KEY: primer_bind
<222> LOCATION: (1566)..(1583)
<223> OTHER INFORMATION: 5AS2 primer bind site
<220> FEATURE:
<221> NAME/KEY: primer_bind
<222> LOCATION: (1584)..(1599)
<223> OTHER INFORMATION: 5C primer bind site
<220> FEATURE:
<221> NAME/KEY: primer_bind
<222> LOCATION: (1720)..(1740)
<223> OTHER INFORMATION: 6UP primer bind site
<220> FEATURE:
<221> NAME/KEY: primer_bind
<222> LOCATION: (2046)..(2068)
<223> OTHER INFORMATION: 6DN primer bind site
<220> FEATURE:
<221> NAME/KEY: primer_bind
<222> LOCATION: (1904)..(1922)
<223> OTHER INFORMATION: 6AS1 primer bind site
<220> FEATURE:
<221> NAME/KEY: primer_bind
<222> LOCATION: (1904)..(1922)
<223> OTHER INFORMATION: 6AS2 primer bind site
<220> FEATURE:
```

```
<221> NAME/KEY: primer_bind
<222> LOCATION: (1923)..(1940)
<223> OTHER INFORMATION: 6C primer bind site
<220> FEATURE:
<221> NAME/KEY: variation
<222> LOCATION: (1922)..(1922)
<223> OTHER INFORMATION: C->T
<220> FEATURE:
<221> NAME/KEY: variation
<222> LOCATION: (1809)..(1809)
<223> OTHER INFORMATION: C-T
<220> FEATURE:
<221> NAME/KEY: variation
<222> LOCATION: (1635)..(1635)
<223> OTHER INFORMATION: C->T
<220> FEATURE:
<221> NAME/KEY: variation
<222> LOCATION: (1095)..(1095)
<223> OTHER INFORMATION: T->C
<220> FEATURE:
<221> NAME/KEY: variation
<222> LOCATION: (1583)..(1583)
<223> OTHER INFORMATION: A->C variation results in an asparagine (N) to
      threonine (T) substitution in the amino acid sequence.

<400> SEQUENCE: 4
atggatctct ggcagctgct gttgaccttg gcagtggcag gctccagtga tgctttttct      60
gggagtgaag ccacaccagc tttccttgtc agagcatctc agagtctgca gatactatat     120
ccagtcctag agacaaattc ttctgggaat cctaaattca ccaagtgccg ttcacctgaa     180
ctggagactt tctcatgtca ctggacagat ggggctaatc acagtttaca gagcccagga     240
tctgtacaga tgttctatat cagaagggac attcaagaat ggaaagaatg ccccgattac     300
gtctctgctg gtgaaaacag ctgttacttt aattcgtctt atacctctgt gtggacccccc    360 tactgcatca agctaactag caatggcggt attgtggatc ataagtgttt ctctgttgag     420
gacatagtac aaccagatcc acccgttggc ctcaactgga ctctactgaa catcagtttg     480
acagagattc atgccgacat cctagtgaaa tgggaaccac cacccaatac agatgttaag     540
atgggatgga taatcctgga gtatgaactg cactataaag aactaaatga gacccagtgg     600
aaaatgatgg accctttaat ggtaacatca gttccgatgt actcgttgag actggataaa     660
gagtatgaag tgcgtgtgag aaccagacaa cgaaacactg aaaaatatgg caagttcagt     720
gaggtgctcc tgataacatt tcctcagatg aacccatctg catgtgaaga gatttccag     780 tttccatggt tcttaattat tatctttgga atacttgggc tagcagtgac attatattta     840
ctcatatttt ctaaacagca aaggattaag atgctgattc tacccccagt tccagttcca     900
aagattaaag gaattgatcc agatctcctc aaggaaggaa aattagaaga ggtgaataca     960
atcttagcca ttcatgacaa ctataaacac gaattctaca atgatgactc ttgggttgaa    1020
tttattgaac tagatattga tgaccctgat gaaaagactg aagggtcaga cacagacaga    1080
cttctgagca atgaccatga aaaatcactc aatatctttg ggcaaaagga tgacgactct    1140
gggcgtacca gctgctatga acctgacatt ctggaggctg atttccatgt cagtgacatg    1200
tgcgatggta cctcagaggt tgctcagcca caaaggttaa aggggaagc agatatctca    1260 tgccttgatc agaagaatca aaataattca ccttctaatg atgctgcccc tgctagccag    1320
cagcccagtg ttatcctagt agaggaaaac aaaccaagac cacttctcat tggtggaact    1380
gagtcaactc atcaagctgt ccatacacag ctcagcaatc caagttcatt ggcaaacatt    1440
gatttttatg cccaggtaag cgacattaca ccagcaggaa atgtggtcct ttccccaggc    1500
caaaagaata agactgggaa cccccagtgt gacacgcacc cagaagtggt cacaccctgc    1560
```

-continued

```
caagctaact tcatcgtgga caacgcttac ttctgcgagg tagacgccaa aaagtacatt    1620
gccctggccc ctcatgtcga ggctgaatca cacatagagc caagctttaa ccaggaagac    1680
atttacatca ccacagaaag ccttaccact cagctggga ggtcggggac agcagaacat     1740
gttccaagtt ctgagatacc tgtcccagat tatacctcca ttcatatagt acagtctcca    1800
cagggcctcg tactcaatgc gactgccctg cccttgcctg acaaagagtt tctctcatca    1860
tgtggctatg tgagcacaga ccaactgaac aaaatcatgc catagctttt ctttgatttc    1920
ctatgagcta cccattgaat ggcacagggt tggctgggc atgaatgctt aaaccaaaac     1980 aatgttttaaa cttttttttgg gaggggggtg agttgagggt ggggaatatg aattctaaat  2040
gccttttcct gaaatgttga acattatat taaaaaaga agaagaatcc ttaatcagat      2100
aaatattcct gttgtgaatt gtaaatactt taaagaactg tctcaaagac tgtttagtgg    2160
cagtaattgt cttgttattg tgggtgttaa ttttgtgcta c                        2201
```

<210> SEQ ID NO 5
<211> LENGTH: 634
<212> TYPE: PRT
<213> ORGANISM: Bos taurus
<220> FEATURE:
<221> NAME/KEY: VARIANT
<222> LOCATION: (528)..(528)
<223> OTHER INFORMATION: N (Asparagine) ->T (threonine)
<220> FEATURE:
<221> NAME/KEY: VARIANT
<222> LOCATION: (279)..(279)
<223> OTHER INFORMATION: Y (tyrosine) ->P (phenylalanine)

<400> SEQUENCE: 5

```
Met Asp Leu Trp Gln Leu Leu Thr Leu Ala Val Ala Gly Ser Ser
1               5                   10                  15

Asp Ala Phe Ser Gly Ser Glu Ala Thr Pro Ala Phe Leu Val Arg Ala
                20                  25                  30

Ser Gln Ser Leu Gln Ile Leu Tyr Pro Val Leu Glu Thr Asn Ser Ser
            35                  40                  45

Gly Asn Pro Lys Phe Thr Lys Cys Arg Ser Pro Glu Leu Glu Thr Phe
        50                  55                  60

Ser Cys His Trp Thr Asp Gly Ala Asn His Ser Leu Gln Ser Pro Gly
65                  70                  75                  80

Ser Val Gln Met Phe Tyr Ile Arg Arg Asp Ile Gln Glu Trp Lys Glu
                85                  90                  95

Cys Pro Asp Tyr Val Ser Ala Gly Glu Asn Ser Cys Tyr Phe Asn Ser
            100                 105                 110

Ser Tyr Thr Ser Val Trp Thr Pro Tyr Cys Ile Lys Leu Thr Ser Asn
        115                 120                 125

Gly Gly Ile Val Asp His Lys Cys Phe Ser Val Glu Asp Ile Val Gln
    130                 135                 140

Pro Asp Pro Pro Val Gly Leu Asn Trp Thr Leu Leu Asn Ile Ser Leu
145                 150                 155                 160

Thr Glu Ile His Ala Asp Ile Leu Val Lys Trp Glu Pro Pro Asn
                165                 170                 175

Thr Asp Val Lys Met Gly Trp Ile Ile Leu Glu Tyr Glu Leu His Tyr
            180                 185                 190

Lys Glu Leu Asn Glu Thr Gln Trp Lys Met Met Asp Pro Leu Met Val
        195                 200                 205

Thr Ser Val Pro Met Tyr Ser Leu Arg Leu Asp Lys Glu Tyr Glu Val
    210                 215                 220
```

```
Arg Val Arg Thr Arg Gln Arg Asn Thr Glu Lys Tyr Gly Lys Phe Ser
225                 230                 235                 240

Glu Val Leu Leu Ile Thr Phe Pro Gln Met Asn Pro Ser Ala Cys Glu
                245                 250                 255

Glu Asp Phe Gln Phe Pro Trp Phe Leu Ile Ile Ile Phe Gly Ile Leu
            260                 265                 270

Gly Leu Ala Val Thr Leu Tyr Leu Leu Ile Phe Ser Lys Gln Gln Arg
            275                 280                 285

Ile Lys Met Leu Ile Leu Pro Pro Val Pro Val Pro Lys Ile Lys Gly
290                 295                 300

Ile Asp Pro Asp Leu Leu Lys Glu Gly Lys Leu Glu Glu Val Asn Thr
305                 310                 315                 320

Ile Leu Ala Ile His Asp Asn Tyr Lys His Glu Phe Tyr Asn Asp Asp
                325                 330                 335

Ser Trp Val Glu Phe Ile Glu Leu Asp Ile Asp Asp Pro Asp Glu Lys
            340                 345                 350

Thr Glu Gly Ser Asp Thr Asp Arg Leu Leu Ser Asn Asp His Glu Lys
            355                 360                 365

Ser Leu Asn Ile Phe Gly Ala Lys Asp Asp Ser Gly Arg Thr Ser
370                 375                 380

Cys Tyr Glu Pro Asp Ile Leu Glu Ala Asp Phe His Val Ser Asp Met
385                 390                 395                 400

Cys Asp Gly Thr Ser Glu Val Ala Gln Pro Gln Arg Leu Lys Gly Glu
                405                 410                 415

Ala Asp Ile Ser Cys Leu Asp Gln Lys Asn Gln Asn Asn Ser Pro Ser
                420                 425                 430

Asn Asp Ala Ala Pro Ala Ser Gln Gln Pro Ser Val Ile Leu Val Glu
            435                 440                 445

Glu Asn Lys Pro Arg Pro Leu Leu Ile Gly Gly Thr Glu Ser Thr His
    450                 455                 460

Gln Ala Val His Thr Gln Leu Ser Asn Pro Ser Ser Leu Ala Asn Ile
465                 470                 475                 480

Asp Phe Tyr Ala Gln Val Ser Asp Ile Thr Pro Ala Gly Asn Val Val
            485                 490                 495

Leu Ser Pro Gly Gln Lys Asn Lys Thr Gly Asn Pro Gln Cys Asp Thr
            500                 505                 510

His Pro Glu Val Val Thr Pro Cys Gln Ala Asn Phe Ile Val Asp Asn
    515                 520                 525

Ala Tyr Phe Cys Glu Val Asp Ala Lys Lys Tyr Ile Ala Leu Ala Pro
    530                 535                 540

His Val Glu Ala Glu Ser His Ile Glu Pro Ser Phe Asn Gln Glu Asp
545                 550                 555                 560

Ile Tyr Ile Thr Thr Glu Ser Leu Thr Thr Thr Ala Gly Arg Ser Gly
                565                 570                 575

Thr Ala Glu His Val Pro Ser Ser Glu Ile Pro Val Pro Asp Tyr Thr
            580                 585                 590

Ser Ile His Ile Val Gln Ser Pro Gln Gly Leu Val Leu Asn Ala Thr
            595                 600                 605

Ala Leu Pro Leu Pro Asp Lys Glu Phe Leu Ser Ser Cys Gly Tyr Val
            610                 615                 620

Ser Thr Asp Gln Leu Asn Lys Ile Met Pro
625                 630
```

```
<210> SEQ ID NO 6
<211> LENGTH: 25
<212> TYPE: DNA
<213> ORGANISM: Bos taurus

<400> SEQUENCE: 6
gtggctatca agtgaaatca ttgac                                          25

<210> SEQ ID NO 7
<211> LENGTH: 25
<212> TYPE: DNA
<213> ORGANISM: Bos taurus

<400> SEQUENCE: 7
actgggttga tgaaacactt cactc                                          25

<210> SEQ ID NO 8
<211> LENGTH: 30
<212> TYPE: DNA
<213> ORGANISM: Bos taurus

<400> SEQUENCE: 8
ccagtttcca tggttcttaa ttattatctt                                     30

<210> SEQ ID NO 9
<211> LENGTH: 30
<212> TYPE: DNA
<213> ORGANISM: Bos taurus

<400> SEQUENCE: 9
ggttatatca cacttacctt tgctgtttag                                     30

<210> SEQ ID NO 10
<211> LENGTH: 20
<212> TYPE: DNA
<213> ORGANISM: Bos taurus

<400> SEQUENCE: 10
cagtgacatt atatttactc                                                20

<210> SEQ ID NO 11
<211> LENGTH: 20
<212> TYPE: DNA
<213> ORGANISM: Bos taurus

<400> SEQUENCE: 11
cagtgacatt attttactc                                                 20

<210> SEQ ID NO 12
<211> LENGTH: 20
<212> TYPE: DNA
<213> ORGANISM: Bos taurus

<400> SEQUENCE: 12
gggctagcag tgacattata                                                20

<210> SEQ ID NO 13
<211> LENGTH: 20
<212> TYPE: DNA
<213> ORGANISM: Bos taurus

<400> SEQUENCE: 13
gggctagcag tgacattatt                                                20
```

```
<210> SEQ ID NO 14
<211> LENGTH: 23
<212> TYPE: DNA
<213> ORGANISM: Bos taurus

<400> SEQUENCE: 14
tttactcata ttttctaaac agc                                            23

<210> SEQ ID NO 15
<211> LENGTH: 20
<212> TYPE: DNA
<213> ORGANISM: Bos taurus

<400> SEQUENCE: 15
gcctcatcat tcactgctta                                                20

<210> SEQ ID NO 16
<211> LENGTH: 20
<212> TYPE: DNA
<213> ORGANISM: Bos taurus

<400> SEQUENCE: 16
ggtttcaaca taaggctctg                                                20

<210> SEQ ID NO 17
<211> LENGTH: 22
<212> TYPE: DNA
<213> ORGANISM: Bos taurus

<400> SEQUENCE: 17
gtcttttgaa atgagaatga gg                                             22

<210> SEQ ID NO 18
<211> LENGTH: 22
<212> TYPE: DNA
<213> ORGANISM: Bos taurus

<400> SEQUENCE: 18
gtcttttgaa atgagaatga gt                                             22

<210> SEQ ID NO 19
<211> LENGTH: 24
<212> TYPE: DNA
<213> ORGANISM: Bos taurus

<400> SEQUENCE: 19
aacttacatc aaaacaaaat tttg                                           24

<210> SEQ ID NO 20
<211> LENGTH: 20
<212> TYPE: DNA
<213> ORGANISM: Bos taurus

<400> SEQUENCE: 20
gcctcatcat tcactgctta                                                20

<210> SEQ ID NO 21
<211> LENGTH: 20
<212> TYPE: DNA
<213> ORGANISM: Bos taurus

<400> SEQUENCE: 21
```
ggtttcaaca taaggctctg                                          20

<210> SEQ ID NO 22
<211> LENGTH: 25
<212> TYPE: DNA
<213> ORGANISM: Bos taurus

<400> SEQUENCE: 22
caaggtaatt aataaaatat ctaag                                    25

<210> SEQ ID NO 23
<211> LENGTH: 25
<212> TYPE: DNA
<213> ORGANISM: Bos taurus

<400> SEQUENCE: 23
caaggtaatt aataaaatat ctaaa                                    25

<210> SEQ ID NO 24
<211> LENGTH: 24
<212> TYPE: DNA
<213> ORGANISM: Bos taurus

<400> SEQUENCE: 24
ttgtacatga cactaattaa atgt                                     24

<210> SEQ ID NO 25
<211> LENGTH: 25
<212> TYPE: DNA
<213> ORGANISM: Bos taurus

<400> SEQUENCE: 25
tcttgggttg aatttattga actag                                    25

<210> SEQ ID NO 26
<211> LENGTH: 24
<212> TYPE: DNA
<213> ORGANISM: Bos taurus

<400> SEQUENCE: 26
atcgcacatg tcactgacat ggaa                                     24

<210> SEQ ID NO 27
<211> LENGTH: 19
<212> TYPE: DNA
<213> ORGANISM: Bos taurus

<400> SEQUENCE: 27
cagacttctg agcaatgac                                           19

<210> SEQ ID NO 28
<211> LENGTH: 19
<212> TYPE: DNA
<213> ORGANISM: Bos taurus

<400> SEQUENCE: 28
cagacttctg agcaatgat                                           19

<210> SEQ ID NO 29
<211> LENGTH: 21
<212> TYPE: DNA
<213> ORGANISM: Bos taurus

<400> SEQUENCE: 29

-continued catgaaaaat cactcaatat c                                        21

<210> SEQ ID NO 30
<211> LENGTH: 25
<212> TYPE: DNA
<213> ORGANISM: Bos taurus

<400> SEQUENCE: 30
acattacacc agcaggaaat gtggt                                    25

<210> SEQ ID NO 31
<211> LENGTH: 24
<212> TYPE: DNA
<213> ORGANISM: Bos taurus

<400> SEQUENCE: 31
tggtaaggct ttctgtggtg atgt                                     24

<210> SEQ ID NO 32
<211> LENGTH: 18
<212> TYPE: DNA
<213> ORGANISM: Bos taurus

<400> SEQUENCE: 32
taacttcatc gtggacac                                            18

<210> SEQ ID NO 33
<211> LENGTH: 18
<212> TYPE: DNA
<213> ORGANISM: Bos taurus

<400> SEQUENCE: 33
taacttcatc gtggacaa                                            18

<210> SEQ ID NO 34
<211> LENGTH: 16
<212> TYPE: DNA
<213> ORGANISM: Bos taurus

<400> SEQUENCE: 34
cgcttacttc tgcgag                                              16

<210> SEQ ID NO 35
<211> LENGTH: 21
<212> TYPE: DNA
<213> ORGANISM: Bos taurus

<400> SEQUENCE: 35
aggtcgggga cagcagaaca t                                        21

<210> SEQ ID NO 36
<211> LENGTH: 23
<212> TYPE: DNA
<213> ORGANISM: Bos taurus

<400> SEQUENCE: 36
tcatattccc caccctcaac tca                                      23

<210> SEQ ID NO 37
<211> LENGTH: 19
<212> TYPE: DNA
<213> ORGANISM: Bos taurus

```
<400> SEQUENCE: 37
agcttttctt tgatttccc                                              19

<210> SEQ ID NO 38
<211> LENGTH: 19
<212> TYPE: DNA
<213> ORGANISM: Bos taurus

<400> SEQUENCE: 38
agcttttctt tgatttcct                                              19

<210> SEQ ID NO 39
<211> LENGTH: 18
<212> TYPE: DNA
<213> ORGANISM: Bos taurus

<400> SEQUENCE: 39
atgagctacc cattgaat                                               18

<210> SEQ ID NO 40
<211> LENGTH: 27
<212> TYPE: DNA
<213> ORGANISM: Bos taurus

<400> SEQUENCE: 40
taggagttcc ttttagagga taggtgc                                     27

<210> SEQ ID NO 41
<211> LENGTH: 22
<212> TYPE: DNA
<213> ORGANISM: Bos taurus

<400> SEQUENCE: 41
gccttgtgga gaagttgaca aa                                          22

<210> SEQ ID NO 42
<211> LENGTH: 22
<212> TYPE: DNA
<213> ORGANISM: Bos taurus

<400> SEQUENCE: 42
gcccagagaa acagcatttc ta                                          22

<210> SEQ ID NO 43
<211> LENGTH: 22
<212> TYPE: DNA
<213> ORGANISM: Bos taurus

<400> SEQUENCE: 43
tcactgccat atttccagca tc                                          22

<210> SEQ ID NO 44
<211> LENGTH: 25
<212> TYPE: DNA
<213> ORGANISM: Bos taurus

<400> SEQUENCE: 44
cttgctcata aaatactcgt gtcct                                       25

<210> SEQ ID NO 45
<211> LENGTH: 23
<212> TYPE: DNA
<213> ORGANISM: Bos taurus
```

```
<400> SEQUENCE: 45
atgcaatggc aaagtcttcc tac                                              23

<210> SEQ ID NO 46
<211> LENGTH: 26
<212> TYPE: DNA
<213> ORGANISM: Bos taurus

<400> SEQUENCE: 46
tgtatgaagt aacttagtcg tcttcg                                           26

<210> SEQ ID NO 47
<211> LENGTH: 22
<212> TYPE: DNA
<213> ORGANISM: Bos taurus

<400> SEQUENCE: 47 gagagggtt gttgaacaca aa                                                22

<210> SEQ ID NO 48
<211> LENGTH: 25
<212> TYPE: DNA
<213> ORGANISM: Bos taurus

<400> SEQUENCE: 48
tcctactttc cagaaattca ttttg                                            25

<210> SEQ ID NO 49
<211> LENGTH: 27
<212> TYPE: DNA
<213> ORGANISM: Bos taurus

<400> SEQUENCE: 49
ctgaggctaa tgtatattga tctggac                                          27

<210> SEQ ID NO 50
<211> LENGTH: 25
<212> TYPE: DNA
<213> ORGANISM: Bos taurus

<400> SEQUENCE: 50
gtggctatca agtgaaatca ttgac                                            25

<210> SEQ ID NO 51
<211> LENGTH: 25
<212> TYPE: DNA
<213> ORGANISM: Bos taurus

<400> SEQUENCE: 51
actgggttga tgaaacactt cactc                                            25

<210> SEQ ID NO 52
<211> LENGTH: 20
<212> TYPE: DNA
<213> ORGANISM: Bos taurus

<400> SEQUENCE: 52
gcctcatcat tcactgctta                                                  20

<210> SEQ ID NO 53
<211> LENGTH: 20
<212> TYPE: DNA
```

<213> ORGANISM: Bos taurus

<400> SEQUENCE: 53
ggtttcaaca taaggctctg                                               20

<210> SEQ ID NO 54
<211> LENGTH: 27
<212> TYPE: DNA
<213> ORGANISM: Bos taurus

<400> SEQUENCE: 54
acatggtttg ttatatgatt ttgttac                                       27

<210> SEQ ID NO 55
<211> LENGTH: 20
<212> TYPE: DNA
<213> ORGANISM: Bos taurus

<400> SEQUENCE: 55
acattctgga ggctgatttc                                               20

<210> SEQ ID NO 56
<211> LENGTH: 20
<212> TYPE: DNA
<213> ORGANISM: Bos taurus

<400> SEQUENCE: 56
caaaagaata agactgggaa                                               20

<210> SEQ ID NO 57
<211> LENGTH: 22
<212> TYPE: DNA
<213> ORGANISM: Bos taurus

<400> SEQUENCE: 57
ttcatattcc ccaccctcaa ct                                            22

<210> SEQ ID NO 58
<211> LENGTH: 20
<212> TYPE: DNA
<213> ORGANISM: Bos taurus

<400> SEQUENCE: 58
agcttggctc tacgtgtgat                                               20

<210> SEQ ID NO 59
<211> LENGTH: 20
<212> TYPE: DNA
<213> ORGANISM: Bos taurus

<400> SEQUENCE: 59
gataacactg ggctgctggt                                               20

<210> SEQ ID NO 60
<211> LENGTH: 25
<212> TYPE: DNA
<213> ORGANISM: Bos taurus

<400> SEQUENCE: 60
tgctctaatc ttttctggta ccagg                                         25

<210> SEQ ID NO 61
<211> LENGTH: 27

```
-continued

<212> TYPE: DNA
<213> ORGANISM: Bos taurus

<400> SEQUENCE: 61
tcctccccaa atcaattaca ttttctc                                         27

<210> SEQ ID NO 62
<211> LENGTH: 104
<212> TYPE: DNA
<213> ORGANISM: Bos taurus
<220> FEATURE:
<221> NAME/KEY: variation
<222> LOCATION: (60)..(60)
<223> OTHER INFORMATION: There is an A/T polymorphism at position 60.

<400> SEQUENCE: 62
ccagtttcca tggttcttaa ttattatctt tggaatactt gggctagcag tgacattata    60
tttactcata ttttctaaac agcaaaggta agtgtgatat aacc                    104
```